(12) United States Patent
Patterson et al.

(10) Patent No.: US 9,168,147 B2
(45) Date of Patent: Oct. 27, 2015

(54) SELF-DEPLOYING LOCKING SCREW RETENTION DEVICE

(71) Applicant: Titan Spine, LLC, Mequon, WI (US)

(72) Inventors: Chad J. Patterson, Port Washington, WI (US); Peter F. Ullrich, Jr., Neenah, WI (US)

(73) Assignee: Titan Spine, LLC, Mequon, WI (US)

( * ) Notice: Subject to any disclaimer, the term of this patent is extended or adjusted under 35 U.S.C. 154(b) by 10 days.

(21) Appl. No.: 13/713,417

(22) Filed: Dec. 13, 2012

(65) Prior Publication Data

US 2013/0123925 A1 May 16, 2013

Related U.S. Application Data

(63) Continuation-in-part of application No. 13/572,077, filed on Aug. 10, 2012, now Pat. No. 8,496,710, which is a continuation of application No. 12/151,198, filed on May 5, 2008, now Pat. No. 8,262,737, and a continuation-in-part of application No. 11/123,359, filed on May 6, 2005, now Pat. No. 7,662,186.

(51) Int. Cl.
*A61B 17/86* (2006.01)
*A61F 2/44* (2006.01)
(Continued)

(52) U.S. Cl.
CPC ............... *A61F 2/442* (2013.01); *A61B 17/844* (2013.01); *A61F 2/4465* (2013.01); *A61F 2/30965* (2013.01); *A61F 2002/2817* (2013.01); *A61F 2002/2835* (2013.01); *A61F 2002/305* (2013.01);
(Continued)

(58) Field of Classification Search
CPC ............ A61F 2002/30092; A61F 2002/30484; A61F 2002/30495; A61F 2002/30039; A61B 17/844
USPC .................................................. 606/300–319
See application file for complete search history.

(56) References Cited

U.S. PATENT DOCUMENTS 4,314,876 A 2/1982 Kremer et al.
4,834,757 A 5/1989 Brantigan
(Continued)

FOREIGN PATENT DOCUMENTS

EP 0599419 6/1994
EP 0916323 5/1999
(Continued)

OTHER PUBLICATIONS

Wennerberg, A., et al., "Effects of titanium surface topography on bone integration: a systematic review", Clin. Oral Impl. Res., 20 (Suppl. 4), 2009, pp. 172-184.
(Continued)

*Primary Examiner* — Ellen C Hammond
(74) *Attorney, Agent, or Firm* — Stradley Ronon Stevens & Young, LLP

(57) ABSTRACT

A screw assembly and a spinal implant. The screw assembly includes a screw with a head and a shaft where a screw retention member is positioned beneath the head of the screw and substantially surrounds the shaft of the screw. The screw retention member is formed from a temperature-sensitive material. The screw retention member has a first contracted position adapted for inserting the screw through at least one hole in the spinal implant and a second expanded position adapted for retaining the screw within the at least one hole in the spinal implant. The screw retention member may be in the form of a coiled spring or a collar having a plurality of tabs.

21 Claims, 19 Drawing Sheets

(51) Int. Cl.
  *A61B 17/84* (2006.01)
  *A61F 2/30* (2006.01)
  *A61F 2/28* (2006.01)
  *A61F 2/46* (2006.01)

(52) U.S. Cl.
  CPC ............ *A61F 2002/30014* (2013.01); *A61F 2002/30039* (2013.01); *A61F 2002/3084* (2013.01); *A61F 2002/30092* (2013.01); *A61F 2002/30133* (2013.01); *A61F 2002/30405* (2013.01); *A61F 2002/30441* (2013.01); *A61F 2002/30443* (2013.01); *A61F 2002/30444* (2013.01); *A61F 2002/30454* (2013.01); *A61F 2002/30469* (2013.01); *A61F 2002/30472* (2013.01); *A61F 2002/30481* (2013.01); *A61F 2002/30484* (2013.01); *A61F 2002/30495* (2013.01); *A61F 2002/30507* (2013.01); *A61F 2002/30566* (2013.01); *A61F 2002/30574* (2013.01); *A61F 2002/30576* (2013.01); *A61F 2002/30578* (2013.01); *A61F 2002/30604* (2013.01); *A61F 2002/30772* (2013.01); *A61F 2002/30785* (2013.01); *A61F 2002/30787* (2013.01); *A61F 2002/30836* (2013.01); *A61F 2002/30892* (2013.01); *A61F 2002/30906* (2013.01); *A61F 2002/30925* (2013.01); *A61F 2002/30973* (2013.01); *A61F 2002/448* (2013.01); *A61F 2002/4475* (2013.01); *A61F 2002/4629* (2013.01); *A61F 2310/00017* (2013.01); *A61F 2310/00023* (2013.01); *A61F 2310/00047* (2013.01); *A61F 2310/00071* (2013.01); *A61F 2310/00077* (2013.01); *A61F 2310/00083* (2013.01); *A61F 2310/00107* (2013.01); *A61F 2310/00149* (2013.01)

(56) References Cited

U.S. PATENT DOCUMENTS

| | | | |
|---|---|---|---|
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |
| 5,571,188 A | 11/1996 | Ellingsen et al. |
| 5,603,338 A | 2/1997 | Beaty |
| 5,609,635 A | 3/1997 | Michelson |
| 5,702,449 A | 12/1997 | McKay |
| 5,755,798 A | 5/1998 | Papavero et al. |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,865,845 A | 2/1999 | Thalgott |
| 5,876,453 A | 3/1999 | Beaty |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlaepfer et al. |
| 6,080,158 A | 6/2000 | Lin |
| 6,086,613 A | 7/2000 | Camino et al. |
| 6,096,107 A | 8/2000 | Caracostas et al. |
| 6,123,705 A | 9/2000 | Michelson |
| 6,143,032 A | 11/2000 | Schafer et al. |
| 6,176,882 B1 | 1/2001 | Biedermann et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 | 6/2001 | Biscup |
| 6,296,664 B1 | 10/2001 | Middleton |
| 6,302,914 B1 | 10/2001 | Michelson |
| 6,342,074 B1 | 1/2002 | Simpson |
| 6,344,057 B1 | 2/2002 | Rabbe et al. |
| 6,350,283 B1 | 2/2002 | Michelson |
| 6,375,681 B1 | 4/2002 | Truscott |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,425,920 B1 | 7/2002 | Hamada |
| 6,432,140 B1 | 8/2002 | Lin |
| 6,436,102 B1 | 8/2002 | Ralph et al. |
| 6,447,544 B1 | 9/2002 | Michelson |
| 6,458,159 B1 | 10/2002 | Thalgott |
| 6,478,823 B1 | 11/2002 | Michelson |
| 6,482,233 B1 | 11/2002 | Aebi et al. |
| 6,485,517 B1 | 11/2002 | Michelson |
| 6,491,723 B1 | 12/2002 | Beaty |
| 6,520,993 B2 | 2/2003 | James et al. |
| 6,558,424 B2 | 5/2003 | Thalgott |
| 6,569,201 B2 | 5/2003 | Moumene et al. |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,964,687 B1 | 11/2005 | Bernard et al. |
| 6,974,480 B2 | 12/2005 | Messerli et al. |
| 6,981,975 B2 | 1/2006 | Michelson |
| 7,018,412 B2 | 3/2006 | Ferreira et al. |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Liu et al. |
| 7,128,760 B2 | 10/2006 | Michelson |
| 7,137,997 B2 | 11/2006 | Paul |
| 7,141,068 B2 | 11/2006 | Ross et al. |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |
| 7,238,186 B2 | 7/2007 | Zdeblick et al. |
| 7,244,275 B2 | 7/2007 | Michelson |
| 7,250,060 B2 | 7/2007 | Trieu |
| 7,255,698 B2 | 8/2007 | Michelson |
| 7,288,093 B2 | 10/2007 | Michelson |
| 7,311,734 B2 | 12/2007 | Van Hoeck et al. |

(56) References Cited

U.S. PATENT DOCUMENTS

| | | |
|---|---|---|
| D564,095 S | 3/2008 | Blain |
| 7,347,873 B2 | 3/2008 | Paul et al. |
| D566,276 S | 4/2008 | Blain |
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 8,262,737 B2 | 9/2012 | Bagga et al. |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0156529 A1 | 10/2002 | Li et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0083668 A1 | 5/2003 | Rogers et al. |
| 2003/0105527 A1 | 6/2003 | Bresina |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0073314 A1 | 4/2004 | White et al. |
| 2004/0117019 A1 | 6/2004 | Trieu et al. |
| 2004/0117020 A1 | 6/2004 | Frey et al. |
| 2004/0122518 A1 | 6/2004 | Rhoda |
| 2004/0127993 A1 | 7/2004 | Kast et al. |
| 2004/0134886 A1 | 7/2004 | Wagner et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0119758 A1 | 6/2005 | Alexander et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1 | 9/2005 | Pope et al. |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1 | 1/2009 | White et al. |
| 2009/0014243 A1 | 1/2009 | Whigham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0076559 A1 | 3/2010 | Bagga et al. |
| 2010/0094426 A1 | 4/2010 | Grohowski, Jr. et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1 | 1/2011 | Ankem |
| 2011/0040301 A1 | 2/2011 | Blain et al. |
| 2011/0082503 A1 | 4/2011 | Blain |
| 2011/0190902 A1 | 8/2011 | Tong et al. |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |

(56) References Cited

U.S. PATENT DOCUMENTS

| | | |
|---|---|---|
| 2012/0172991 A1 | 7/2012 | Bertele et al. |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |
| 2013/0310883 A1* | 11/2013 | Levy et al. ............ 606/313 |
| 2014/0094860 A1* | 4/2014 | Reimels ............... 606/323 |
| 2014/0309691 A1* | 10/2014 | Brown et al. .......... 606/232 |

FOREIGN PATENT DOCUMENTS

| | | |
|---|---|---|
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Pending U.S. Appl. No. 13/286,813 of Chad J. Patterson, et al., filed Nov. 1, 2011.
Pending U.S. Appl. No. 13/826,304 of Peter F. Ullrich, Jr., et al., filed Mar. 14, 2013.
Pending U.S. Appl. No. 13/713,417 of Chad J. Patterson, et al., filed Dec. 13, 2012.
Pending U.S. Appl. No. 13/784,144 of Peter F. Ullrich, Jr., et al., filed Mar. 4, 2013.
Astra Tech Dental, "Nanolevel topographic modifications on the OsseoSpeed surface", http://shop.dentsplyimplants.us, Mar. 8, 2001.
Astra Tech Dental, "OsseoSpeed—more bone more rapidly", http://shop.dentsplyimplants.us, May 2011.
Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.
He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.
Isa, et al., "Effects of Fluoride-Modified Titanium Surfaces on Osteoblast Proliferation and Gene Expression", Int. J. Oral Maxillofac. Implants 2006; 21:203-211.
Lamolle, et al., "The effect of hydrofluoric acid treatment of titanium surface on nanostructural and chemical changes and the growth of MC3T3-E1 cells", Biomaterials 30 (Nov. 20, 2008) 736-742.
Meirelles, et al., "The Effect of Chemical and Nanotopographical Modifications on the Early Stages of Osseointegration", Int. J. Oral Maxillofac. Implants 2008; 23:641-647.
Supplementary Partial European Search Report issued Sep. 27, 2011.
Supplementary Partial European Search Report issued Aug. 19, 2011.
Variola, et al., "Nanoscale surface modifications of medically relevant metals: state-of-the art and prespectives", Nanoscale, 2011, 3, 335-353.
Wennerberg, et al., "Spontaneously formed nanostructures on titanium surfaces", Clin. Oral Impl. Res., 2012, 1-7.
Petrini, et al., "Biomedical Applications of Shape Memory Alloys", J. Metallurgy, vol. 2011, (2011) Article ID 501483, pp. 1-15.

* cited by examiner

SELF-DEPLOYING LOCKING SCREW RETENTION DEVICE

CROSS REFERENCE TO RELATED APPLICATIONS

This application is a continuation-in-part of U.S. patent application Ser. No. 13/572,077, which is a continuation of U.S. patent application Ser. No. 12/151,198, filed on May 5, 2008, which issued as U.S. Pat. No. 8,262,737, which is a continuation-in-part of U.S. patent application Ser. No. 11/123,359, filed on May 6, 2005, and issued as U.S. Pat. No. 7,662,186. The contents of all prior applications are incorporated by reference into this document, in their entirety and for all purposes.

TECHNICAL FIELD

The present invention relates generally to interbody spinal implants and, more particularly, to spinal implants having bone screws with a self-deploying screw retention device.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

Some of the common problems with spinal implants include movement or expulsion of the implant once inserted between adjacent vertebrae. In particular, when the flexible tissue (the annulus) connecting the disks is severed in the surgical procedure additional vertical and lateral instability in the joint is induced. In order to reduce implant movement or expulsion from between the vertebral bodies, spinal implants may be affixed to adjacent vertebrae, for example, using additional fixation elements, such as screws. The use of additional fixation outside of the joint space, for example, by using screws and plates, screws and rods, or screws alone can limit the amount of displacement that occurs as the vertebra move away from one another reducing movement and activity. Unfortunately, screws can loosen, back out, and even break over time.

A number of screw retention or secondary screw fixation devices are available to try to combat the problem of back out. For example, a screw locking plate and fastener assembly may be placed over the heads of the screws or a snap or c-clip may be embedded into the implant body. Typical screw retention devices rigidly fix the screws within the device. This rigidity does not allow for movement of the screws, however, and can result in increased loading in the joint space. In other words, the loading can create pressure points where the screws are located and can produce undesired bone remodeling at those locations. Similarly, implants having aggressive teeth or ridges can remodel the bone around these sharp features providing instability and movement in the joint assembly. Rigid fixation, increased loading and pressure points, and movement and instability of the implant can result in mechanical failure of the screws. Mechanical failure of the screws and associated pieces of the screw retention devices (e.g., screw locking plate, c-clip, etc.) places the patient at risk for unsecured screws and the like in the vertebral disk space. Thus, there remains a need for a screw retention mechanism which secures the screw, but does not create any of the problems mentioned above for traditional screw retention devices.

SUMMARY OF THE INVENTION

To meet this and other needs, and in view of its purposes, the present invention provides for interbody spinal implants having one or more screws with a self-deploying screw retention member. The implants, screws, and screw retention devices of the present invention are designed and selected such that the screws may be secured in a manner that does not change the loading of the implant and adds stability and expulsion resistance to the implant. The screws and self-deploying retention mechanisms work in concert with the fusion-enhancing implant and the bone structure-preserving surgical technique described in this document. In particular, the locations and alignment of the screws (e.g., based on screw insertion path), final location within the disk space, and friction between the integration surface(s) of the implant and the preserved vertebral endplates reduce the potential for joint motion-induced loosening and back out of the screws.

In addition, the screw retention members are self-deploying and are integrated with the screws adding to ease of use and reducing the likelihood of additional fragments in the disk space in the unlikely event of screw failure. In use, the screws may be fastened to the implant and the bone with the screw retention members in a contracted or retracted position.

After implantation (e.g., once the implant reaches body temperature), the screw retention members may expand to lock the screws in place and prevent the screws from backing out of position.

Various implant body shapes are provided to allow for implantation through various access paths to the spine through a patient's body. Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion.

In one embodiment, the present invention provides an interbody spinal implant assembly comprising an interbody spinal implant and at least one screw. The spinal implant may include a top surface, a bottom surface, opposing lateral sides, and opposing anterior and posterior portions where at least one of the top surface and bottom surface has a roughened surface topography, without sharp teeth that risk damage to bone structures, adapted to grip bone through friction generated when the implant is placed between two vertebrae and to inhibit migration of the implant. At least one hole, which is sized and configured to receive a screw, extends through the implant. The one or more holes in the implant may include a retaining feature, such as a ridge or protrusion, adapted to engage the screw retention member when in the expanded position.

According to another embodiment, the present invention provides a screw assembly for a spinal implant comprising a screw having a head and a shaft. The screw retention member (e.g., a coiled spring or a collar with a plurality of tabs) is positioned beneath the head of the screw and at least partially surrounds the shaft of the screw. The screw includes a screw retention member comprising a temperature-sensitive or thermal-responsive material. The screw retention member may have a first contracted position adapted for inserting the screw through at least one hole in the spinal implant and a second expanded position adapted for retaining the screw within the at least one hole in the spinal implant.

The screw retention member may be of any suitable shape and size. In one embodiment, the screw retention member is in the shape of a coiled spring or a collar with a plurality of petals or tabs, for example. In the case of the coiled spring, the screw retention member may comprise the spring coiled around the shaft and positioned beneath the head of the screw. In the contracted position, a portion of the spring proximate to the head of the screw may have a first diameter and, in the expanded position, the portion of the spring proximate to the head of the screw may have a second diameter greater than the first diameter. In the contracted position, a portion or substantially all (e.g., the interior portion) of the spring may contact the shaft of the screw and, in the second expanded position, at least a portion of the spring may not contact the shaft of the screw and may contact the head of the screw.

The screw retention member may be in the shape of a collar with a plurality of petals or tabs. For example, the collar with a plurality of tabs may partially, substantially, or completely surround the shaft of the screw and may be positioned beneath the head of the screw. In the contracted position, the plurality of tabs may approximately contour to the shape of the head of the screw and, in the expanded position, the plurality of tabs may protrude at an angle of about 80-110° (e.g., about 90°) relative to the shaft.

The retention member may be formed from a temperature-sensitive metal alloy, for example, where the retention member is deployed when the implant is raised to or above the transformation temperature of the temperature-sensitive metal alloy (e.g., at or slightly below body temperature). In addition or in the alternative, the retention member may be formed from a shape memory material. For example, the retention member may be formed from nickel-containing alloys (e.g., nickel-titanium alloys, such as nitinol), titanium-containing alloys (e.g., titanium-palladium alloys), copper-containing alloys (e.g., copper-aluminum-nickel or copper-zinc alloys), iron-containing alloys (e.g., iron-platinum alloys), and the like.

According to another embodiment, the present invention provides a method of deploying at least one screw retention member in a spinal implant comprising: (a) inserting at least one screw comprising a screw retention member in a first contracted position into a hole of a spinal implant, wherein the screw retention member is formed from a temperature-sensitive material have a transformation temperature; and (b) allowing the screw retention member to deploy into a second expanded position retaining the screw within the hole of the spinal implant when the temperature-sensitive material reaches the transformation temperature.

The top surface, bottom surface, or both surfaces of the implant, which may be defined as integration surfaces, may have a roughened surface topography. The integration surface(s) may have fusion and biologically active surface geometry, for example, in regular repeating patterns. The integration surface(s) may include macro features, micro features, and nano features. For example, the features may include a repeating pattern of smooth shapes oriented in opposition to the biologic forces on the implant and to the insertion direction.

The roughened surface topography may be fabricated, for example, using macro processing, micro processing, and nano processing techniques. The macro, micro, and nano process may include mechanical or chemical removal of at least a portion of the surface. For example, the macro features may be formed by heavy mechanical or chemical bulk removal, the micro features may be formed by mechanical or chemical removal, and the nano features may be formed by mild chemical etching, laser or other directed energy material removal, abrasion, blasting, or tumbling.

For example, the macro features may have a mean spacing between about 400-2,000 microns, a maximum peak-to-valley height between about 40-500 microns, and an average amplitude between about 20-200 microns; the micro features may have a mean spacing between about 20-400 microns, a maximum peak-to-valley height between about 2-40 microns, and an average amplitude between about 1-20 microns; and the nano features may have a mean spacing between about 0.5-20 microns, a maximum peak-to-valley height between about 0.2-2 microns, and an average amplitude between about 0.01-1 microns.

The implant and the screws may be fabricated from any suitable material. For example, the implant or the screws may be comprised of a metal, such as titanium. In the case of a composite implant (e.g., a body with one or more integration plates), the implant body may be fabricated from a non-metallic material, non-limiting examples of which include polyetherether-ketone, hedrocel, ultra-high molecular weight polyethylene, and combinations thereof. The implant body may be fabricated from both a metal and a non-metallic material to form a composite implant. For example, a composite implant may be formed with integration plates made of titanium combined with a polymeric body.

The implant may comprise a substantially hollow center and a vertical aperture. For example, the vertical aperture may (a) extend from the top surface to the bottom surface, (b) have a size and shape predetermined to maximize the surface area of the top surface and the bottom surface available proximate the anterior and posterior portions while maximizing both radiographic visualization and access to the substantially hollow center, and (c) define a transverse rim.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1A:
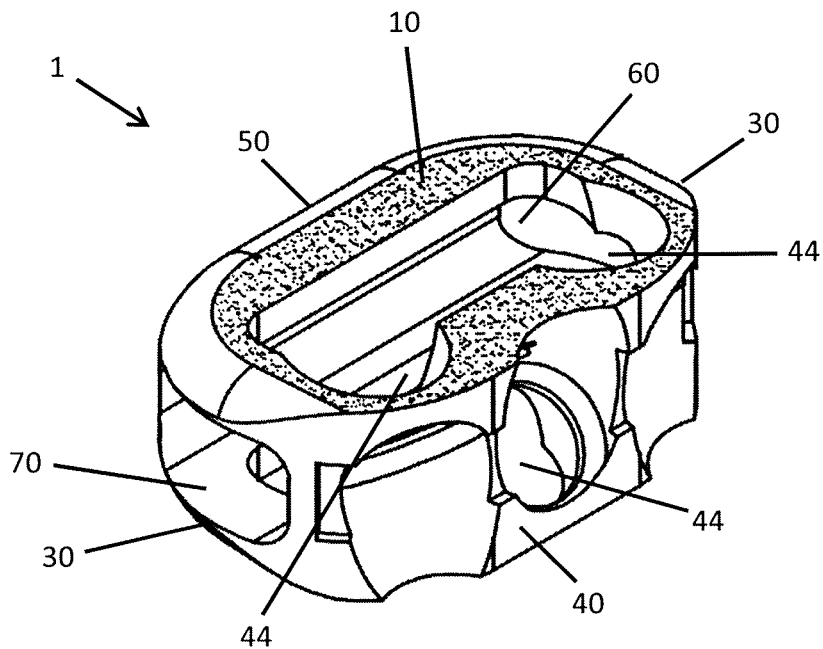
FIG. 1A shows a perspective view of an embodiment of an interbody spinal implant having three through holes.

The present invention provides for spinal implants having screws with a self-deploying screw retention member. The screw retention member is designed to open, extend, or self-deploy, for example, once the retention member reaches near or about body temperature.

According to one embodiment, the present invention provides a screw assembly for a spinal implant comprising a screw having a head and a shaft and a screw retention member (e.g., a coiled spring or a collar with a plurality of tabs) positioned beneath the head of the screw and substantially surrounding the shaft of the screw. The screw retention member may have a contracted or retracted position adapted for inserting the screw through at least one hole in the spinal implant and an expanded position adapted for retaining the screw within the at least one hole in the spinal implant.

Screw Retention Member

The screw includes at least one self-deploying retention member. As used in this document, "self-deploying" includes a screw retention member or a portion of the screw retention member that deploys, expands, or extends once a certain condition is met (e.g., temperature sensitive or shape memory). The screw retention member does not require any type of physical or manual manipulation in order to be deployed. In other words, the screw retention member deploys by itself when the necessary condition is met. The screw retention member may be in a "contracted" or "retracted" condition, state, or position meaning that the screw retention member is unobtrusive and permits the screw to be inserted into or removed from the screw opening or hole in the implant. The screw retention member may be in a "deployed" condition, state, or position meaning that the retention member or a portion of the retention member extends or opens to lock the screw into position such that the screw cannot be inserted into or removed from the screw opening or hole. In other words, the screw is retained in the hole of the implant such that the screw cannot back out.

The screw retention member may be formed from a temperature-sensitive material (e.g., a thermal reactive shape memory material) or a mechanical shape-memory material, for example. As will be recognized by one of ordinary skill in the art, temperature-sensitive materials and shape-memory materials are capable of remembering a previously memorized shape or position. In the case of a temperature-sensitive or thermal-reactive material, the screw retention member remains in a contracted state until the retention member is raised to or above a given temperature, for example, the transformation temperature of a temperature-sensitive metal alloy. The transformation temperature is a temperature at which a change in phase occurs. For example, the temperature-sensitive material can transition between martensite and austenite phases. Thus, the temperature-sensitive material may be deformed (e.g., placed in a contracted position) in the martensite phase where it will remain deformed until heated to the austenite phase where it will return to its pre-deformed shape (e.g., move to a deployed position). In other words, once the screw retention member is raised to or above the transformation temperature, the retention member is deployed and returns to its memorized shape. It is also possible to return the screw retention member to the contracted position (e.g., in the case where the screw needs to later be removed) by lowering the temperature so the retention member returns to the martensite phase (deformed shape).

The transformation temperature may be any temperature above room temperature (above about 20-25° C. (68-77° F.)) up to and including about body temperature (37.0° C.±about 0.5° C. (98.6° F.±about 0.9° F.)), for example. The exact transformation temperature depends on the material selected (e.g., the nickel/titanium ratio of the alloy). Preferably, the transformation temperature ranges from about 25° C. to about 37° C., and more preferably about 30° C. to about 37° C. The shape-memory materials behave in a similar manner, but the condition that causes change may be revealing or exposing the portion of the retention member to be deployed. For example, the retention member may be held in the contracted position (e.g., by a sleeve) and the retention member may be deployed when the sleeve is removed and the screw is secured to the vertebrae.

The screw retention member or any portion of the screw retention member may be formed from any suitable temperature-sensitive or shape-memory material. For example, the retention member may be formed from nickel-containing alloys (e.g., nickel-titanium alloys, such as nitinol), titanium-containing alloys (e.g., titanium-palladium alloys), copper-containing alloys (e.g., copper-aluminum-nickel or copper-zinc alloys), iron-containing alloys (e.g., iron-platinum alloys), and the like. In an exemplary embodiment, the entire screw retention member is formed from a nickel-titanium alloy, such as thermo-reactive nitinol.

The screw retention member may be of any suitable shape and size. Referring now to the drawing, in which like reference numbers refer to like elements throughout the various figures that comprise the drawing, the screw retention member may be in the shape of a coiled spring 62 (FIG. 3) or a collar 64 with a plurality of petals or tabs 66 (FIG. 8), for example. The coiled or helical spring 62 may be comprised of a length of temperature-sensitive material formed into the shape of a helix. The coiled spring 62 may have a suitable cross section, such as a circular, oval, square, or rectangular cross section, for example. The coiled spring 62 may have an inner diameter and an outer diameter, which may be the same or of varying dimensions, for example, depending on whether the spring 62 is in the first retracted or contracted position 54 or in the second expanded or extended position 56.

The collar 64, plurality of petals or tabs 66, or both may also be comprised of temperature-sensitive material. The collar 64 may have a suitable cross section, such as a circular, oval, square, or rectangular cross section, for example. The tabs 66 may also be of a suitable shape, for example, triangular, rectangular, or the like. In an exemplary embodiment, the collar 64 comprises a substantially circular cross section with the plurality of tabs 66 extending from one end of the collar 64. In one embodiment, the tabs 66 are narrowest at the portion connecting to the collar 64 and widest at the tips of the tabs 66 opposite to the connecting portions. Any suitable number and configuration of tabs may be selected so long as the tabs 66 operate to retain the screw 72 in position once the retention member is in the expanded position 56. For example, the collar 64 may include about 5-10 tabs 66 spaced about equidistantly around the circumference of the collar 64. As shown in FIGS. 8(b) and 8(e), the collar 64 may not be connected to form a complete circular cross section. In other words, an expansion gap 67 may be provided, for example, to accommodate different sized shafts 76 of screws 72.

Figure 3:
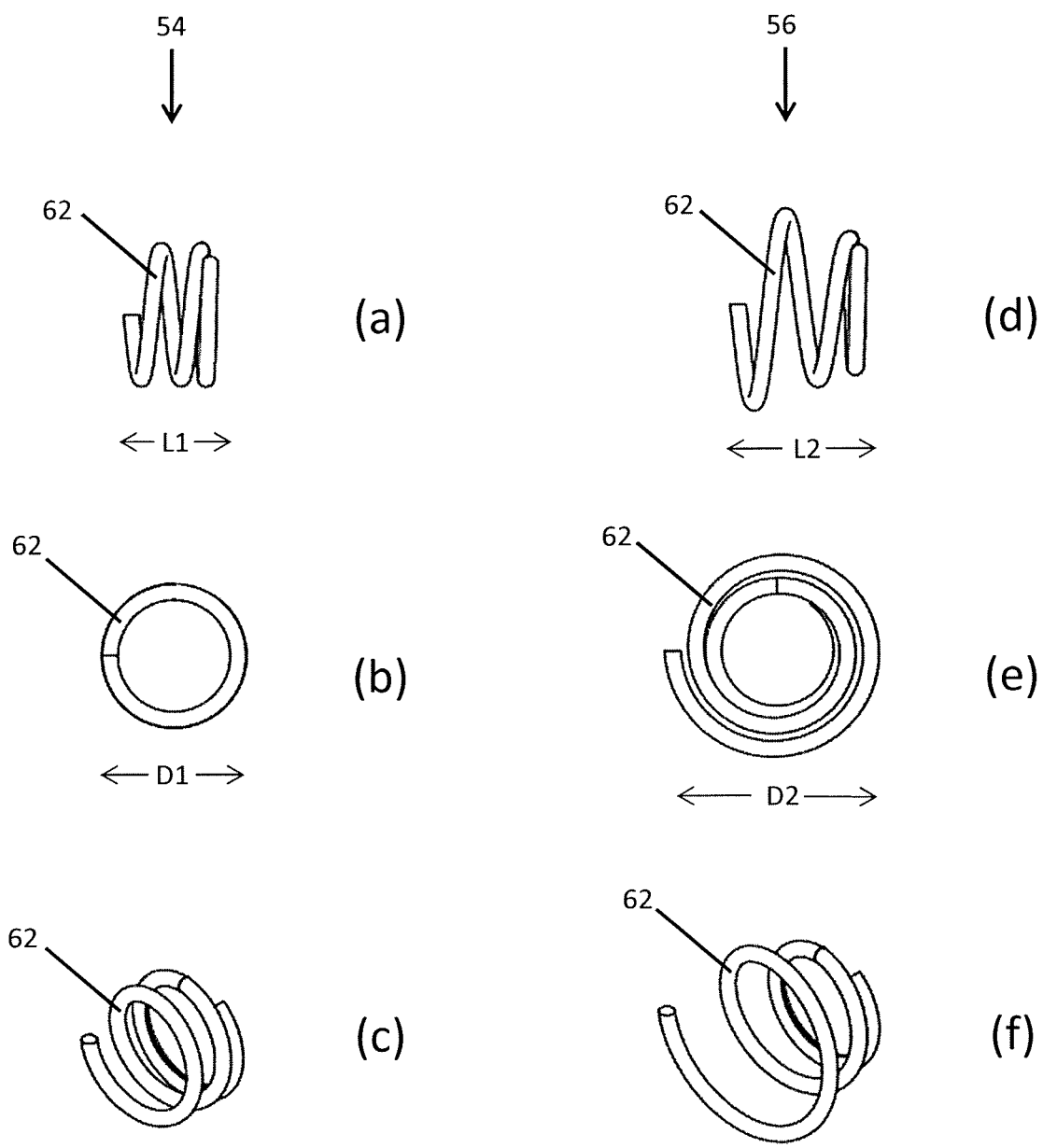
FIG. 3 shows the screw retention device in the form of a coiled spring where (a) is a side view, (b) is a top view, and (c) is a perspective view of the spring in the contracted position and (d) is a side view, (e) is a top view, and (f) is a perspective view of the spring in the expanded position.
Figure 4A:
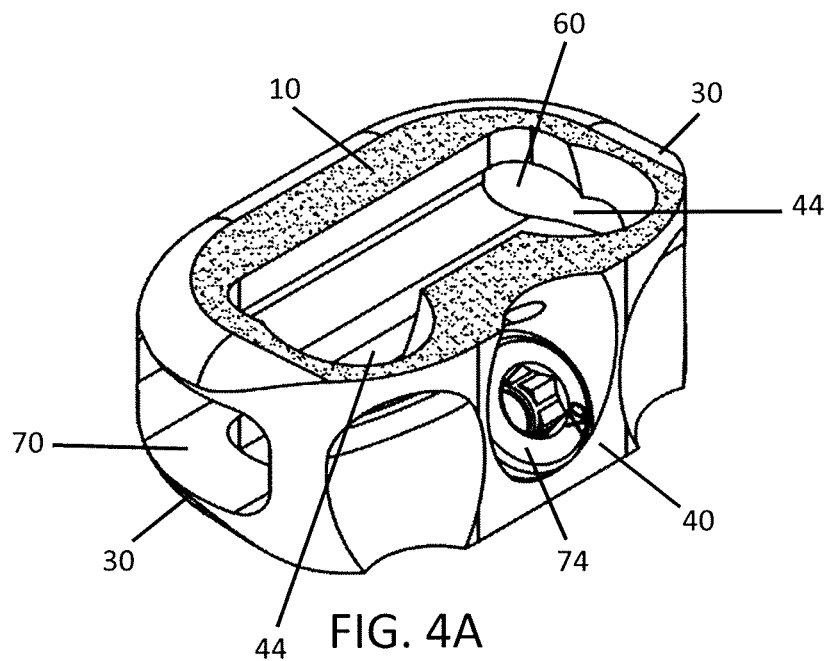
FIG. 4A shows a perspective view of an embodiment of an interbody spinal implant having one screw extending through the implant.
Figure 4B:
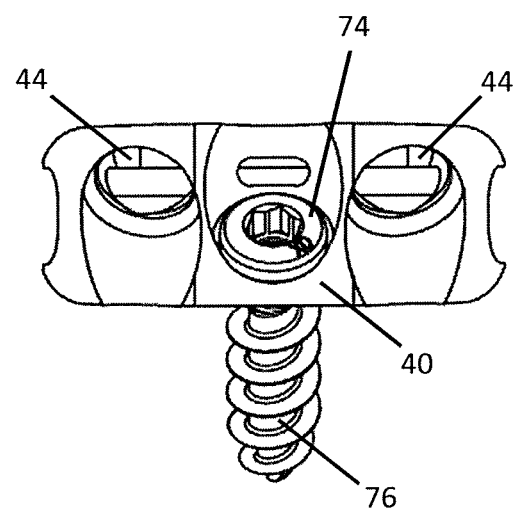
FIG. 4B is a front (anterior) view of the embodiment depicted in FIG. 4A.
Figure 8:
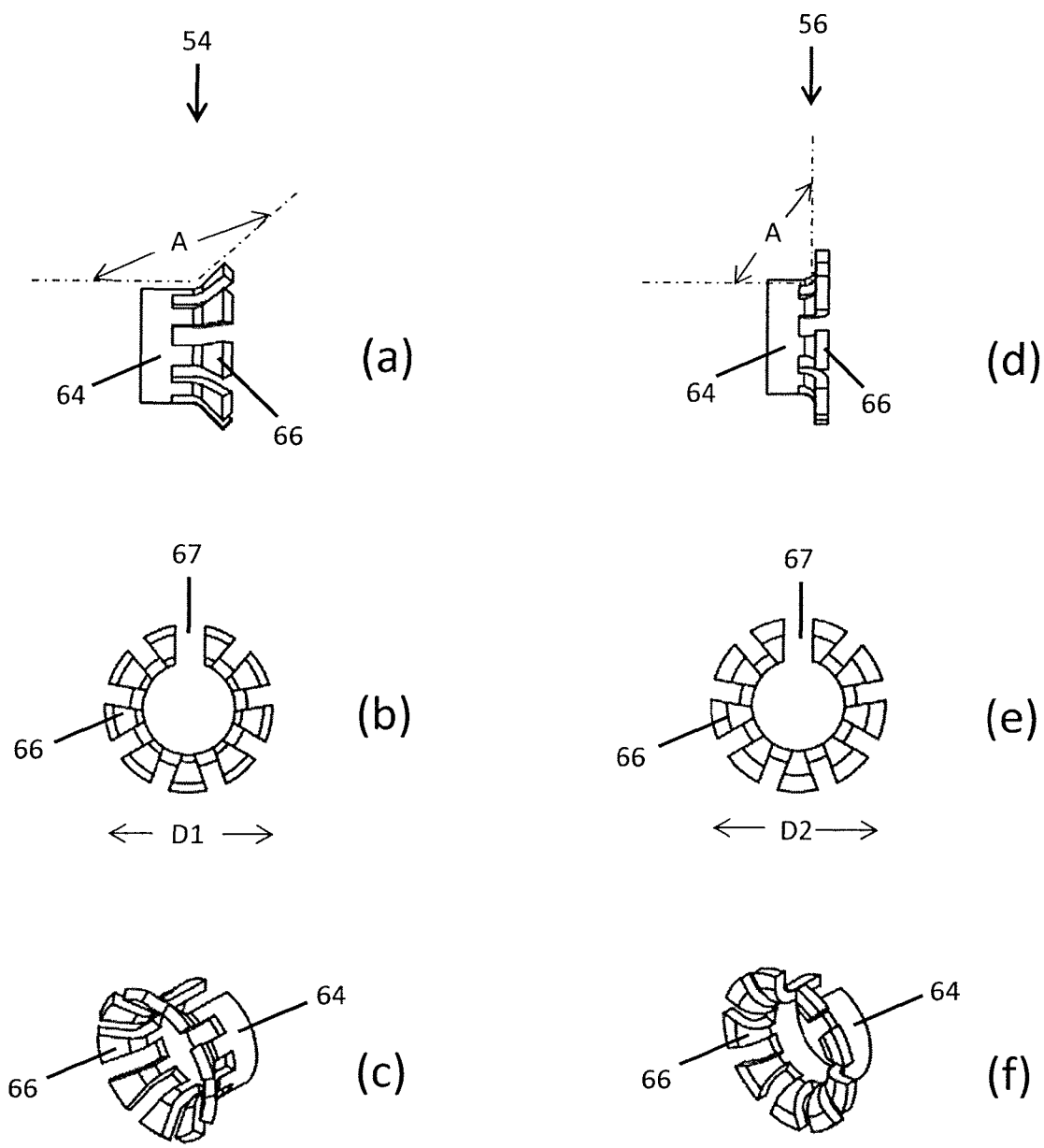
FIG. 8 shows the screw retention device in the form of a collar with a plurality of tabs where (a) is a side view, (b) is a top view, and (c) is a perspective view of the tabs in the contracted position and (d) is a side view, (e) is a top view, and (f) is a perspective view of the tabs in the expanded position.

The contracted position 54 of the screw retention member enables the screw 72 to be inserted through or removed from at least one hole 44 in a spinal implant 1. The expanded position 56 of the screw retention member retains the screw 72 within the hole 44 in the spinal implant 1 and prevents the screw 72 from backing out of position. FIG. 3 depicts the coiled spring 62, which may be used as a screw retention member, where (a) is a side view, (b) is a top view, and (c) is a perspective view of the spring 62 in the contracted position 54 and (d) is a side view, (e) is a top view, and (f) is a perspective view of the spring 62 in the expanded position 56. FIG. 8 shows the screw retention device in the form of a collar 64 with a plurality of tabs 66 where (a) is a side view, (b) is a top view, and (c) is a perspective view of the tabs 66 in the contracted position 54 and (d) is a side view, (e) is a top view, and (f) is a perspective view of the tabs 66 in the expanded position 56. Although a coiled spring 62 and a collar 64 with tabs 66 are exemplified in this document as suitable screw retention members, any suitable configuration and shape for a screw retention member may be selected by one of ordinary skill in the art so long as the retention member can move between the contracted position 54 and the expanded position 56.

Screw Assembly

Although a screw 72 is exemplified in this document, any type of fastener, such as screws, pins, rivets, bolts, nails, or the like may be used to secure the spinal implant 1 to the adjacent vertebrae. The screw 72 may be of any type and size known in the art suitable for use in spinal implants 1. The screw 72 may be comprised of a head 74 and a shaft 76 where at least a portion of the shaft 76 contains threads 78. The size and shape of the head 74 and the shaft 76 and the type of thread 78, including the spacing, diameter, and pitch, are not especially restricted and may be selected by one of ordinary skill in the art for use in spinal implants 1. The head 74 is preferably sized and configured to be retained within the hole 44 in the implant 1. The screw retention member may be positioned, for example, substantially around the shaft 76 and beneath the head 74 of the screw 72.

Figure 2A:
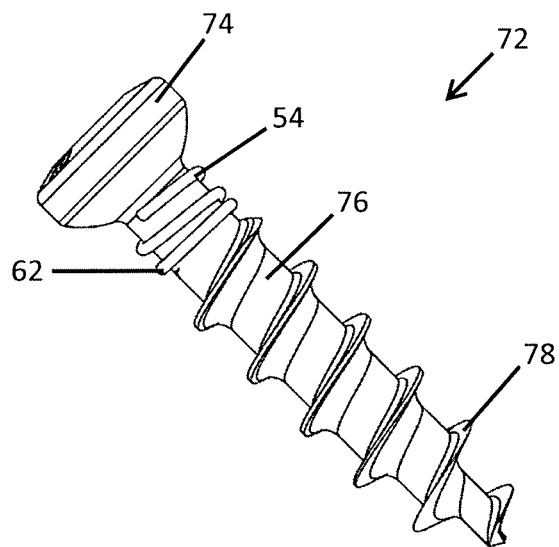
FIG. 2A shows a perspective view of an embodiment of a screw assembly with a screw retention device in the form of a coiled spring in a contracted position.
Figure 2B:
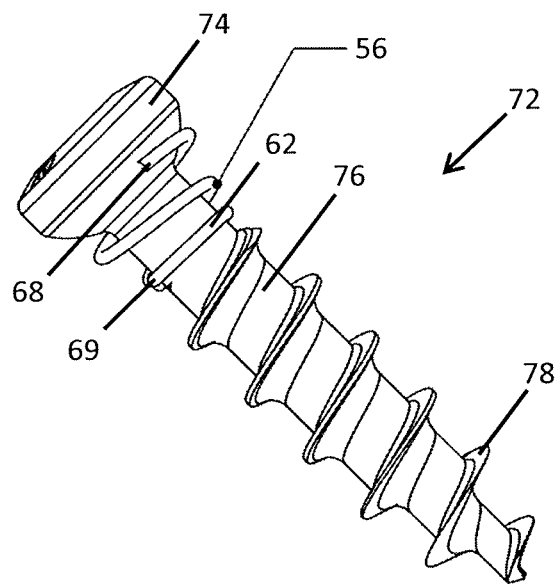
FIG. 2B shows a perspective view of the embodiment depicted in FIG. 2A with the screw retention device in an expanded position.
Figure 5:
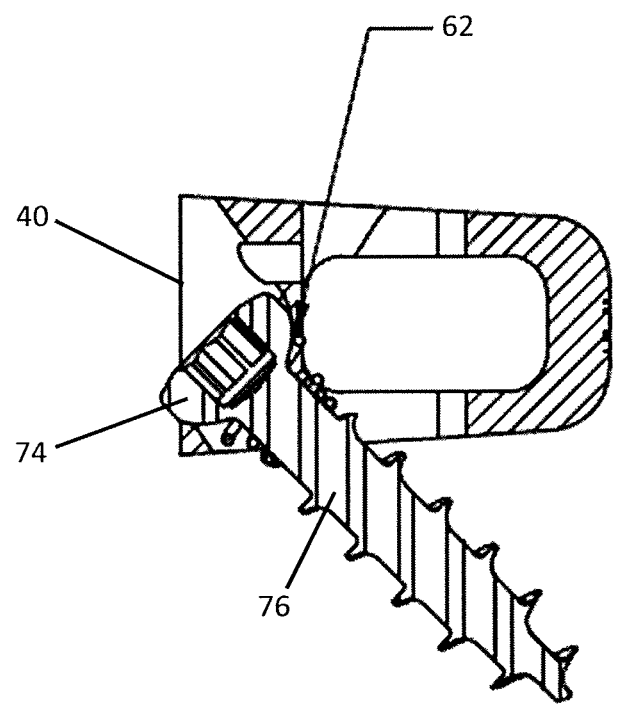
FIG. 5 shows a cross-sectional view of the embodiment depicted in FIG. 4A where the retention member is a coiled spring.

As depicted in FIGS. 2A, 2B, and 5, the screw retention member may comprise the spring 62 coiled substantially or completely around the shaft 76 and positioned beneath the head 74 of the screw 72. In the contracted or retracted position 54, a portion of the spring 62 proximate to the head 74 of the screw 72 may have a first diameter D1 (e.g., an inner diameter), and in the expanded position 56, the portion of the spring 62 proximate to the head 74 of the screw 72 may have a second diameter D2 greater than the first diameter D1 (i.e., D2>D1). In addition, in the contracted position 54, the spring 62 may have a length L1 and, in the expanded position 56, the spring 62 may have a second length L2 greater than the first length L1 (i.e., L2>L1). In the contracted position 54, a substantial portion or substantially all (e.g., the interior portion) of the spring 62 may contact the shaft 76 of the screw 72 and, in the expanded position 56, at least a portion (e.g., the interior portion) of the spring 62 may not contact the shaft 76 of the screw 72 and may at least partially contact the head 74 of the screw 72. In other words, in the expanded position 56, there may be two points of contact to lock the screw 72 into place, a first point of contact 68 where the spring 62 contacts the screw hole 44 (e.g., the retaining tab or ridge 46 on the screw hole 44) and a second point of contact 69 where the spring 62 contacts the thread 78 of the screw 72.

Figure 6A:
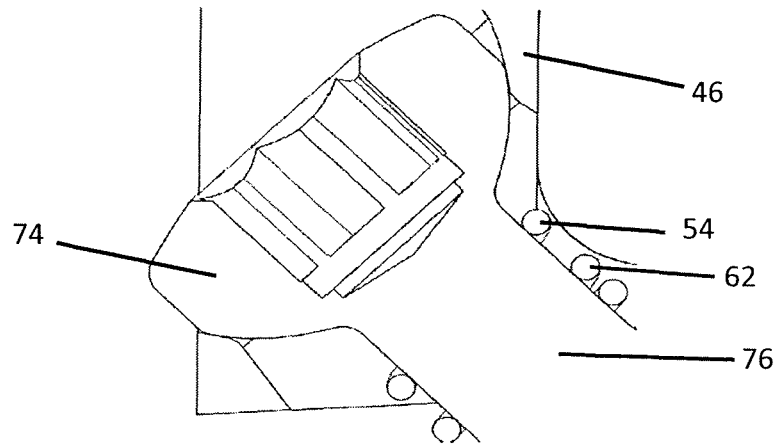
FIG. 6A shows a close-up view of the screw assembly with the screw retention device in the form of a coiled spring in a contracted position.
Figure 6B:
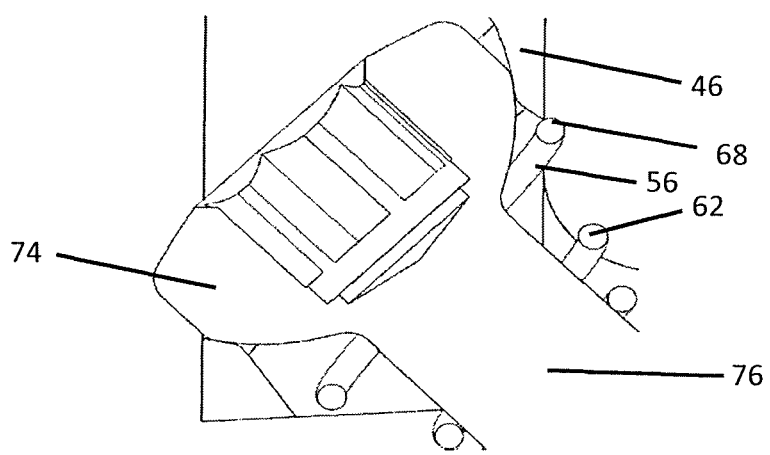
FIG. 6B shows a close-up view of the screw assembly with the screw retention device in the form of a coiled spring in an expanded position.

A close-up view of the screw assembly is shown in FIGS. 6A and 6B. In FIG. 6A, the coiled spring 62 is in the contracted position 54. In FIG. 6B, the coiled spring 62 is in the deployed or expanded position 56. The hole 44 in the implant 1 may include a retaining feature 46 to engage the screw retention member once deployed and in the expanded configuration 56. In FIG. 6A, the screw 72 and coiled spring 62 (in the contracted position 54) are able to traverse the hole 44 in the implant 1. Once in the expanded configuration 56, as shown in FIG. 6B, the screw retention member and the retaining feature 46 engage and prevent the spring 62 from passing back through the screw hole 44 (e.g., prevent back out of the screw 72).

Figure 7A:
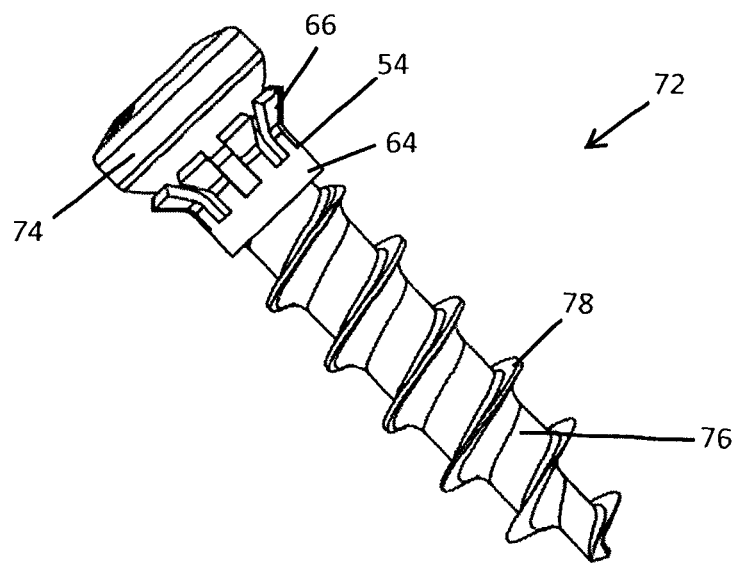
FIG. 7A shows a perspective view of an embodiment of a screw assembly with a screw retention device in the form of a collar with a plurality of tabs in a contracted position.
Figure 7B:
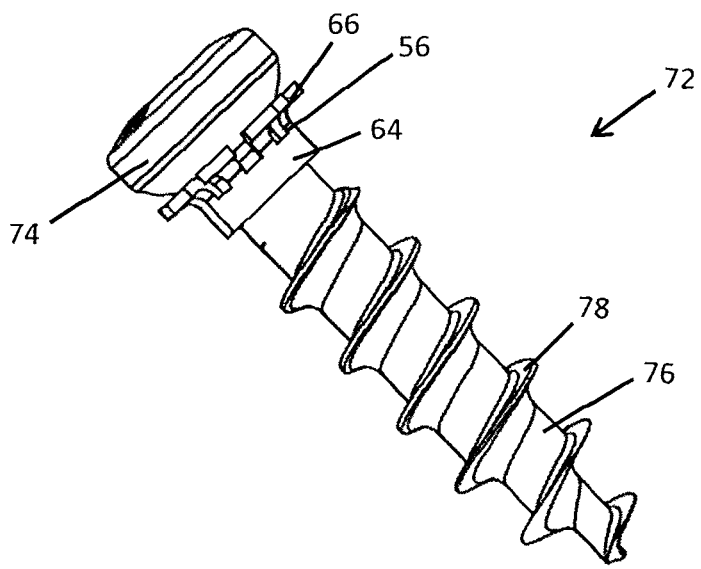
FIG. 7B is a perspective view of the embodiment depicted in FIG. 7A with the screw retention device in an expanded position.
Figure 9:
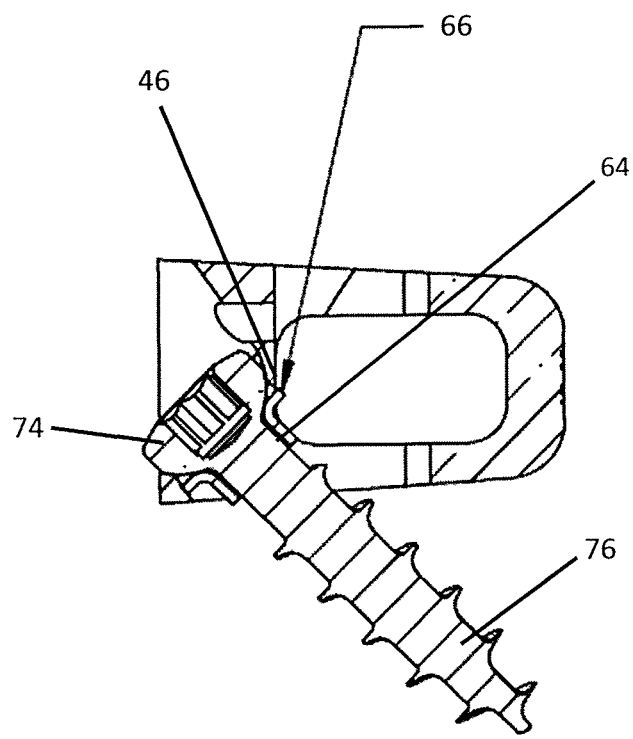
FIG. 9 shows a cross-sectional view of the embodiment depicted in FIG. 7A where the retention member is a collar with a plurality of tabs.

As depicted in FIGS. 7A, 7B, and 9, the screw retention member may be in the shape of a collar 64 with a plurality of tabs 66. The collar 64 may at least partially, substantially, or completely surround the shaft 76 of the screw 72 and may be positioned beneath the head 74 of the screw 72. In the contracted position 54, as best shown in FIG. 7A, the plurality of tabs 66 may approximately contour to the shape of the head 74 (e.g., the outside diameter of the head 74) of the screw 72 (e.g., positioned at an angle A, greater than 90°, preferably greater than 110° shown in FIG. 8(a)). Thus, in the contracted position 54, the screw 72 is able to transverse the opening or hole 44 in the implant 1. In the expanded position 56, the plurality of tabs 66 may protrude at the angle A relative to the shaft 76 (see FIG. 8(d)). For example, once deployed, the tabs 66 may protrude relative to the shaft 76 at the angle A of about 80-110° (e.g., about 90°). In addition, in the contracted position 54, the portion of the tabs 66 proximate to the head 74 of the screw may have a first diameter D1 and, in the expanded position 56, the portion of the tabs 66 proximate to the head 74 of the screw 72 may have a second diameter D2 greater than the first diameter D1 (i.e., D2>D1). In other words, the tabs 66 expand to be bigger than the diameter of the hole 44.

Figure 10A:
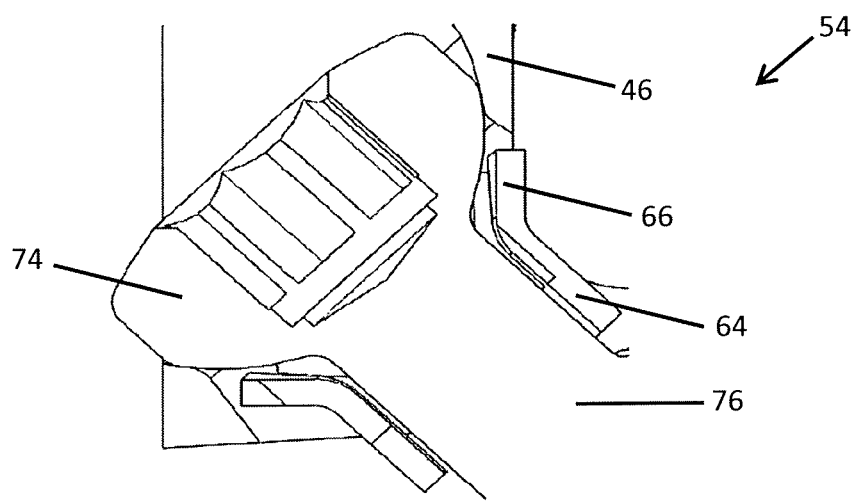
FIG. 10A shows a close-up view of the screw assembly with the screw retention device in the form of a collar with a plurality of tabs in a contracted position.
Figure 10B:
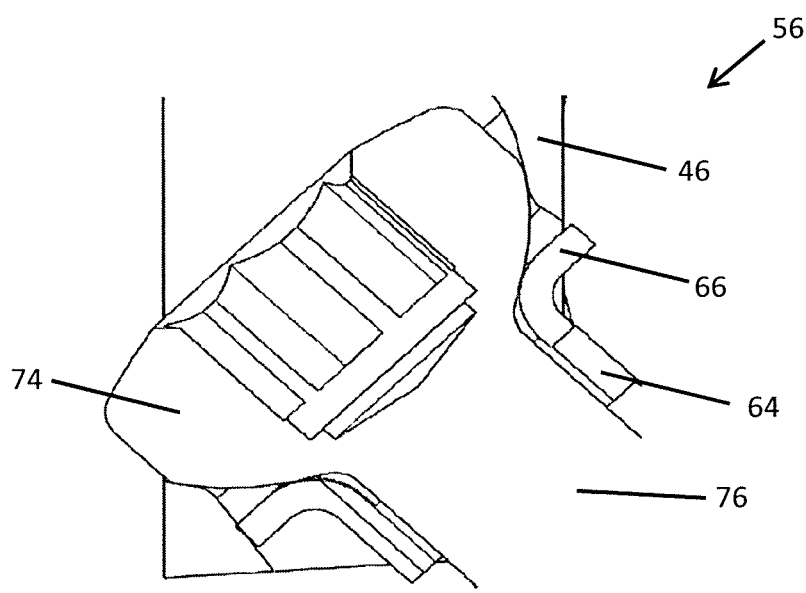
FIG. 10B shows a close-up view of the screw assembly with the screw retention device in the form of a collar with a plurality of tabs in an expanded position.

A close-up view of the screw assembly is shown in FIGS. 10A and 10B. In FIG. 10A, the tabs 66 are in the contracted position 54. In FIG. 10B, the tabs 66 are in the deployed or expanded position 56. The retaining feature 46 is able to engage the screw retention member once deployed and in the expanded configuration 56. In FIG. 10A, the screw 72 and collar 64 having tabs 66 (in the contracted position 54) are able to traverse the hole 44 in the implant 1. Once in the expanded configuration 56, as shown in FIG. 10B, the screw retention member and the retaining feature 46 engage and prevent the tabs 66 from passing back through the screw hole 44 (e.g., prevent back out of the screw 72).

The retention member may or may not be affixed to the screw 72. If attached, any portion of the retention member may be affixed using any suitable attachment mechanisms, such as a pin, a weld, or the like. In addition, each portion of the screw assembly and the screw retention member may or may not be coupled together in any suitable manner and configuration. Each piece of the retention member may be directly connected together or may be coupled together through one or more intervening elements. All portions of the retention member may be formed from a single piece of material (e.g., nitinol) or one or more portions of the retention member may be connected together via soldering, welding, or the like. In a multiple piece construction, the screw retention member may not be coupled to the screw 72, which allows the screw retention member to move freely about the shaft 76 of the screw 72.

The retention member may also be sized or shaped so that it can be assembled to the screw 72 without modifying existing screw designs. A relief or slot 67 may be cut in the body of the retention member allowing the retention member to expand over the diameter of the shaft 76 the screw 72, or the retention member may be sized to thread onto the screw 72. This assembly method also allows for the retention member to engage the threads 78 of the screw 72 to provide for opposing load of the mechanism retaining the screw 72 inside of the implant body. This forms the two points of contact 68, 69 for the locking mechanism.

Implants

The spinal implant 1, 101, 101a, 201, and 301 includes a top surface 10, 110, 110a, 210, and 310, a bottom surface 20, 120, 120a, 220, and 320, opposing lateral sides 30, 130, 130a, 230, and 330, and opposing anterior 40, 140, 140a, 240, and 340 and posterior 50, 150, 150a, 250, and 350 portions. The implant 1, 101, 101a, 201, and 301 may be of any suitable shape. For example, the body of the implant 1, 101, 101a, 201, and 301 may have a generally oval shape, a generally rectangular shape, a generally curved shape, or any other shape described or exemplified in this specification.

Certain embodiments of the interbody implant 1 have a generally oval-shaped transverse cross-sectional area (e.g., FIG. 1A), which may be suitable for Anterior Lumbar Interbody Fusion (ALIF). The implant 101 may have a generally rectangular transverse cross-sectional area (e.g., FIG. 12A) suitable for PLIF. The implant 101a may have a generally curved shape (e.g., FIG. 13A) suitable for TLIF fusion. The implant 201 may be generally circular in shape (e.g., FIG. 14) suitable for cervical fusion. The implant 301 may be generally rectangular in shape (e.g., FIG. 16) suitable for lateral lumbar insertion. The implant 1, 101, 101a, 201, and 301 may be shaped to reduce the risk of subsidence, and improve stability, by maximizing contact with the apophyseal rim of vertebral endplates. Embodiments may be provided in a variety of anatomical footprints and sizes.

Figure 1B:
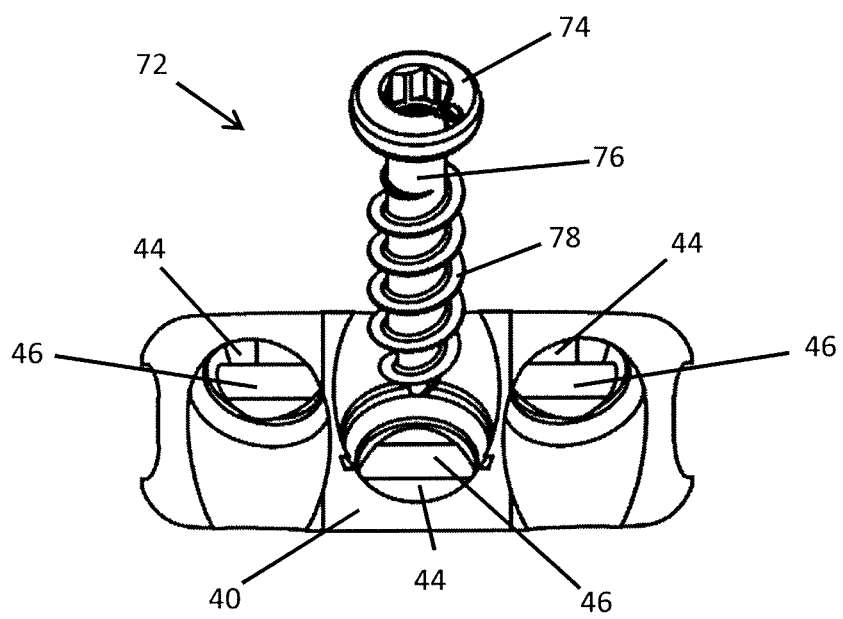
FIG. 1B is a front (anterior) view of the embodiment depicted in FIG. 1A.

The interbody spinal implant 1, 101, 101a, 201, and 301 may include one or more through holes 44 or openings to allow the screw 72 to affix the implant 1, 101, 101a, 201, and 301 to an adjacent vertebrae. As best depicted in FIGS. 1A and 1B, the implant 1 may include one or more screw holes 44 sized and configured to receive the bone screw 72 and to retain the head 74 of the screw 72 in the screw hole 44. The one or more holes 44 should be positioned to provide for access by the surgeon and maximum fixation between the implant 1 and the vertebrae. For an ALIF implant 1, for example, the one or more holes 44 may be positioned on the face of the anterior portion 40 of the implant 1 and may extend through the top surface 10 or bottom surface 20 of the implant 1. In one embodiment, the holes 44 and the corresponding insertion path of the screws 72 are positioned at an angle (e.g., about 30-60°) relative to the anterior portion 40. In a preferred embodiment, at least one hole 44 is positioned to allow one screw 72 to contact the upper vertebrae (e.g., extending through top surface 10) and at least one additional hole 44 is positioned to allow one screw 72 to contact the lower vertebrate (e.g., extending through bottom surface 20). FIGS. 1A and 1B depict one hole 44 extending from the anterior portion 40 at an angle through the implant 1 to the bottom surface 20 and two holes 44 extending from the anterior portion 40 at an angle through the implant 1 to the top surface 10. Although only exemplified in FIG. 1A for implant 1, it will be appreciated by one of ordinary skill in the art that the implants 101, 101a, 201, and 301 may also include one or more holes 44 to allow fixation to adjacent vertebrae with one or more screws 72.

The hole 44 may include the retaining feature 46, which may function to (1) prevent the head 74 of the screw 72 from passing through the hole 44; and (2) act as a stop to engage the screw retention member (e.g., spring 62 or tabs 66 on collar 64) once deployed and in the expanded configuration 56. The retaining feature 46 may include a bar, a tab, a ridge, or the like across or adjacent to the screw hole 44. As depicted in FIGS. 6B and 10B, respectively, once in the expanded configuration 56, the retaining feature 46 may help to prevent the spring 62 or the tabs 66 on the collar 64 from passing back through the screw hole 44 (i.e., preventing back out).

The implant 1, 101, 101a, 201, and 301 may comprise one or more apertures (see, e.g., FIGS. 11A, 11B, 12A, 12B, 13A, 13B, 14, 15, and 16). For example, the implant 1, 101, 101a, 201, and 301 may comprise one or more apertures which extend through the body of the implant 1, 101, 101a, 201, and 301. The implant 1, 101, 101a, 201, and 301 may include one or more vertical apertures 60, 160, 160a, 260, and 360 extending through the main body of the implant 1, 101, 101a, 201, and 301, respectively. In an exemplary embodiment, the implant 1, 101, 101a, 201, and 301 includes a single vertical aperture 60, 160, 160a, 260, and 360 which (a) extends from the top surface 10, 110, 110a, 210, and 310 to the bottom surface 20, 120, 120a, 220, and 320, (b) has a size and shape predetermined to maximize the surface area of the top surface 10, 110, 110a, 210, and 310 and the bottom surface 20, 120, 120a, 220, and 320 available proximate the anterior 40, 140, 140a, 240, and 340 and posterior 50, 150, 150a, 250, and 350 portions while maximizing both radiographic visualization and access to the substantially hollow center, and optionally (c) defines a transverse rim 100, 200a, and 300.

Figure 11A:
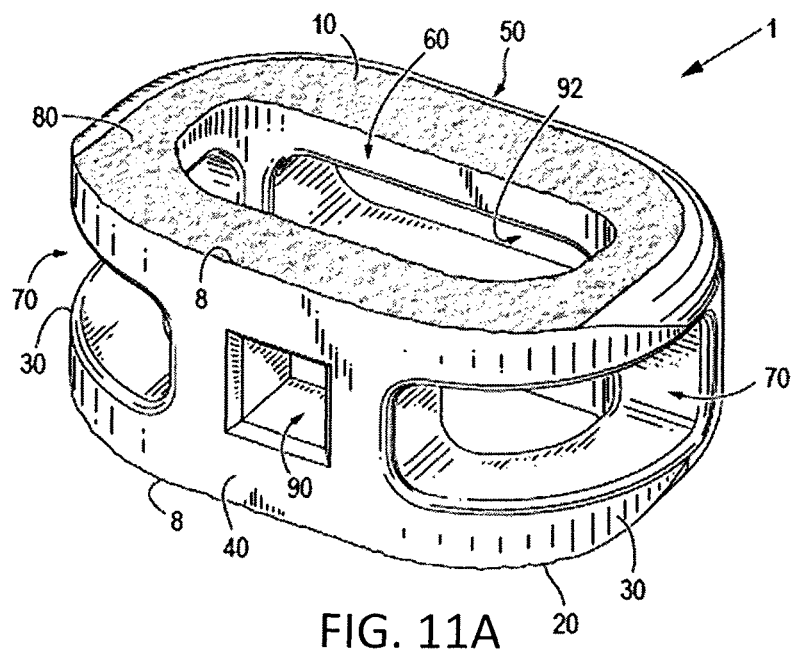
FIG. 11A shows a perspective view of an embodiment of the interbody spinal implant having a generally oval shape and roughened surface topography on the top surface.
Figure 11B:
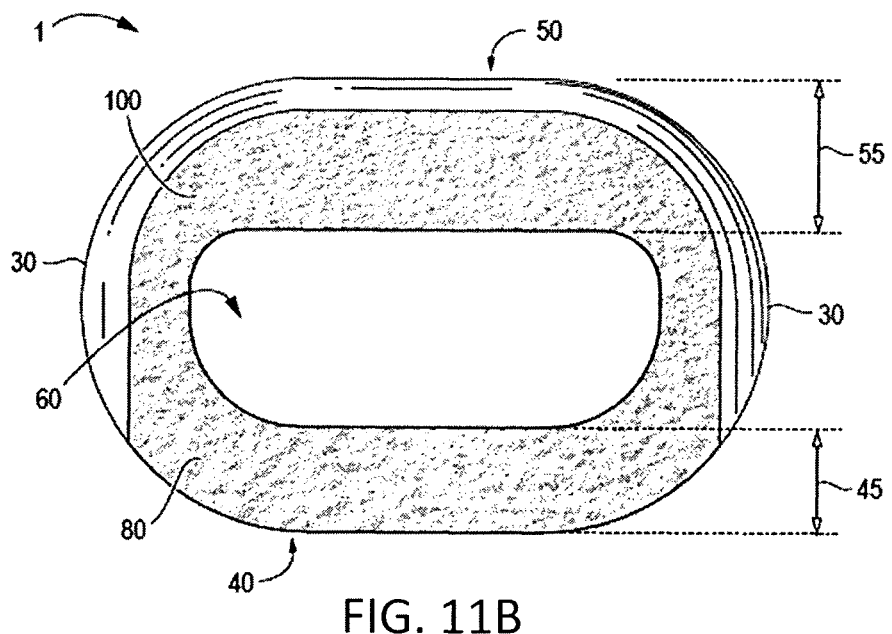
FIG. 11B shows a top view of the embodiment of the interbody spinal implant illustrated in FIG. 11A.

The transverse rim 100 defined by the vertical aperture 60 may have a greater posterior portion thickness 55 than an anterior portion thickness 45 (see, e.g., FIGS. 11A and 11B). In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

Figure 13A:
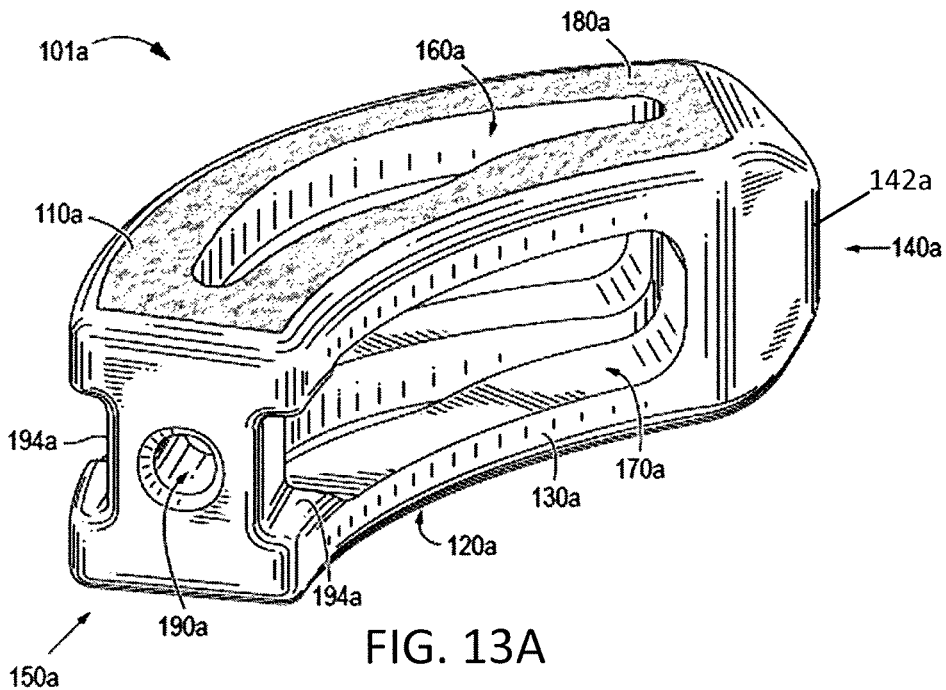
FIG. 13A shows a perspective view from the front of another embodiment of the interbody spinal implant according to the present invention.
Figure 14:
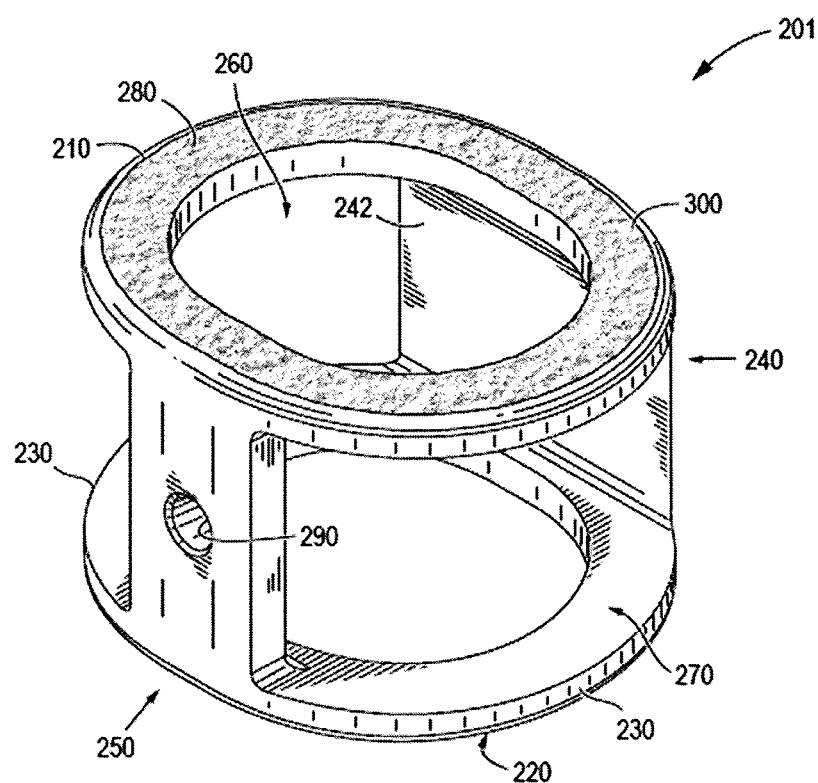
FIG. 14 shows a perspective view of an embodiment of the interbody spinal implant having a generally oval shape and being especially well adapted for use in a cervical spine surgical procedure.

FIG. 13A illustrates a perspective view of the implant 101a with a curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 100) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, the center of the vertical aperture 160a, which defines the maximum width of the vertical aperture 160a, is increased (from 5 mm for the implant 101) to about 7 mm. FIG. 14 illustrates a perspective view of the implant 201 where vertical aperture 260 further defines the transverse rim 300. In one example, the vertical aperture 60, 160, 160a, 260, and 360 may define the transverse rim 100, 200a, and 300 with a varying width or thickness, and having a maximum width at its center, between the opposing lateral sides 30, 130, 130a, 230, and 330, ranging between about 55% and 64% of the distance between the opposing lateral sides 30, 130, 130a, 230, and 330 and tapering inwardly from the center to each of its ends, one end proximate the anterior portion 40, 140, 140a, 240, and 340 and the other end proximate the posterior portion 50, 150, 150a, 250, and 350.

Certain embodiments of the interbody implant 1, 101, 101a, 201, and 301 are substantially hollow. Substantially hollow, as used in this document, means at least about 33% of the interior volume of the interbody spinal implant 1, 101, 101a, 201, and 301 is vacant. The substantially hollow portion may be filled, for example, with cancellous autograft bone, allograft bone, demineralized bone matrix (DBM), porous synthetic bone graft substitute, bone morphogenic protein (BMP), or combinations of those materials.

The implant 1, 101, 101a, 201, and 301 may further comprise one or more transverse apertures 70, 170, 170a, and 270. The transverse aperture 70, 170, 170a, and 270 may extend the entire transverse length of the body of the implant 1, 101, 101a, 201, and 301. The transverse aperture 70, 170, 170a, and 270 may provide improved visibility of the implant 1, 101, 101a, 201, and 301 during surgical procedures to ensure proper implant placement and seating, and may also improve post-operative assessment of implant fusion. The transverse aperture 70, 170, 170a, and 270 may be broken into two, separate sections by an intermediate wall. Suitable shapes and dimensions for the transverse aperture 70, 170, 170a, and 270 may be selected by one of ordinary skill in the art. In particular, all edges of the transverse aperture 70, 170, 170a, and 270 may be rounded, smooth, or both. The intermediate wall may be made of the same material as the remainder of the body of the implant 1, 101, 101a, 201, and 301 (e.g., titanium), or it may be made of another material (e.g., plastic). The intermediate wall may offer one or more of several advantages, including reinforcement of the implant 1, 101, 101a, 201, and 301 and improved bone graft containment.

In the alternative, the implant 1, 101, 101a, 201, and 301 may comprise a solid body, for example, containing no apertures or openings extending through the implant 1, 101, 101a, 201, and 301 (e.g., in the vertical or transverse directions) other than the holes 44 needed for the screws 72. The implants 1, 101, 101a, 201, and 301 may also contain openings (e.g., an opening 90), however, in one or more surfaces of the implant 1, 101, 101a, 201, and 301, for example, for manipulation by tools and the like.

Figure 15:
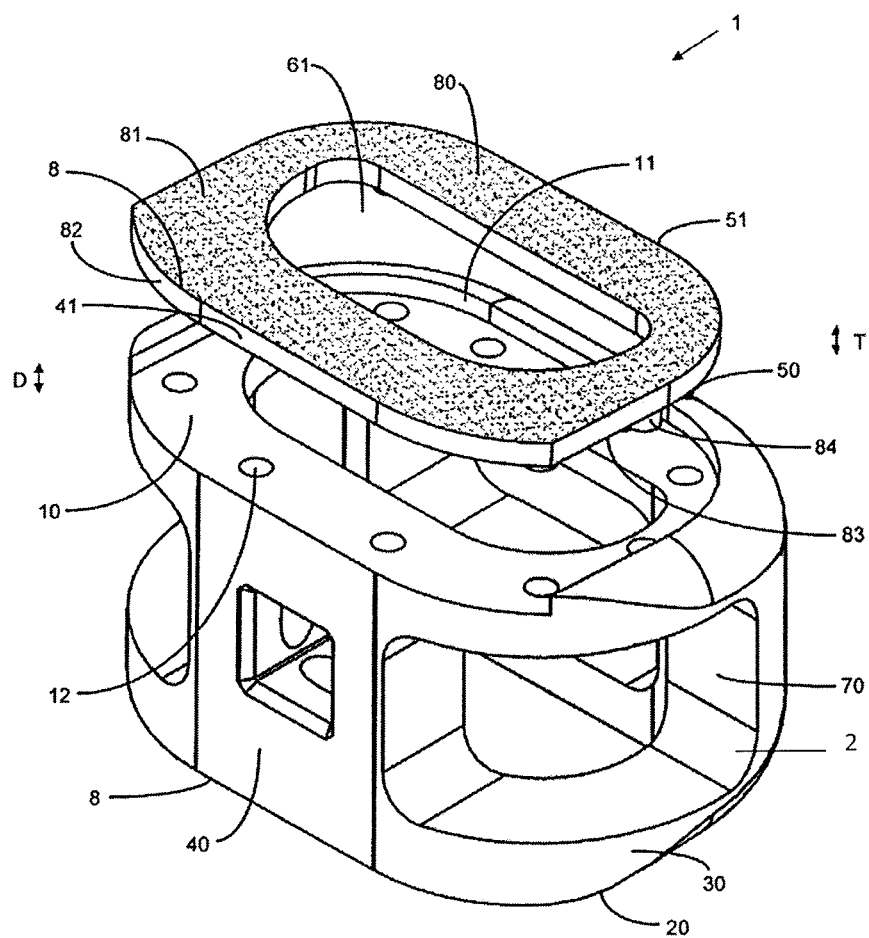
FIG. 15 shows an exploded view of a generally oval-shaped implant with an integration plate.
Figure 16:
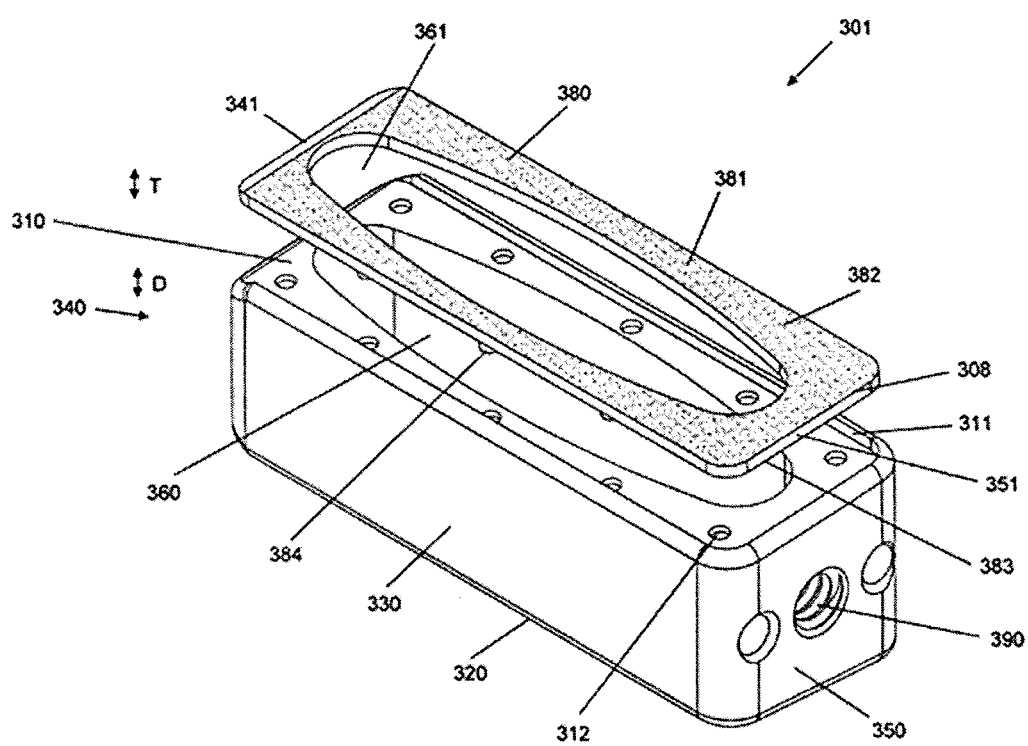
FIG. 16 shows an exploded view of a lateral lumbar implant with an integration plate.

The implant 1, 101, 101a, 201, and 301 may be formed from a single material or may be formed as a composite made from more than one type of material. As depicted in FIGS. 15 and 16, a composite implant 1, 101, 101a, 201, and 301 may comprise one or two integration plates 82, 382, for example. The implant 1, 101, 101a, 201, and 301 may include a first integration plate 82, 382 affixed to the top surface 10, 310 of the body 2 and an optional second integration plate 82, 382 (not shown) affixed to the bottom surface 20, 320 of the body 2. The first integration plate 82, 382 and optional second integration plate 82, 382 each have a top surface 81, 381; a bottom surface 83, 383; opposing lateral sides; opposing anterior portions 41, 341 and posterior portions 51, 351; and a single vertical aperture 61, 361 extending from the top surface 81, 381 to the bottom surface 83, 383 and aligning with the single vertical aperture 60, 360 of the body 2, when present. In the case of a composite implant 1, 101, 101a, 201, and 301 with one or more integration plates 82, 382, the top surface 81, 381 would be the outer surface or integration surface of the implant 1, 101, 101a, 201, and 301. Preferably, the integration plate 82, 382 should be designed to be compatibly shaped and match the dimensions of the body 2 of the implant 1, 101, 101a, 201, and 301. In a composite implant 1, 101, 101a, 201, and 301, the components may be permanently assembled together.

The integration plate 82, 382 may be attached or affixed to the main body 2 of the implant 1, 101, 101a, 201, and 301 using any suitable mechanisms known in the art, for example, a reciprocal connector structure (such as a plurality of posts 84, 384 and holes 12, 312 depicted in FIGS. 15 and 16), fasteners (e.g., a pin, screw, bolt, rod, anchor, snap, clasp, clip, clamp, or rivet), compatibly shaped joints, compatibly shaped undercuts, and/or other suitable connectors having different shapes, sizes, and configurations. An adhesive (e.g., cement, glue, polymer, epoxy, solder, and weld) may also be used to further strengthen any connections described in this specification. The top surface 10, 310 or bottom surface 20, 320 may be recessed at a depth D to allow a thickness T of the integration plate 82, 382 to recess within and form a substantially contiguous outer surface. Recessing the top surface 10, 310 or bottom surface 20, 320 exposes a ridge 11, 311 against which the anterior portion 41, 341, posterior portion 51, 251 or lateral side of the integration plate 82, 382 may be seated when brought together with the implant 1, 301.

Figure 12A:
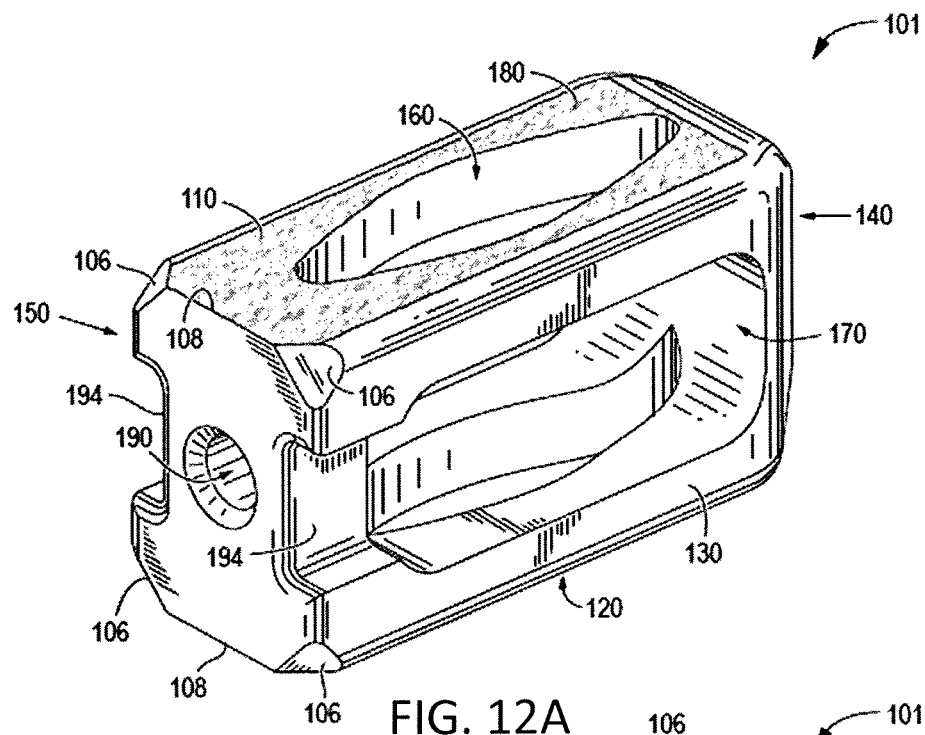
FIG. 12A shows a perspective view from the front of another embodiment of the interbody spinal implant according to the present invention.
Figure 12B:
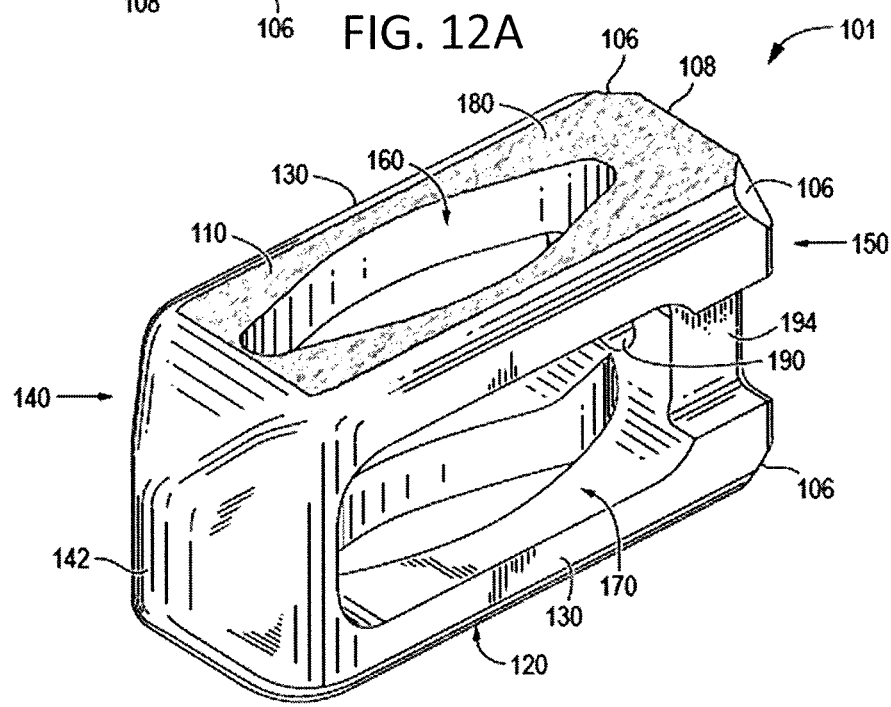
FIG. 12B shows a perspective view from the rear of the embodiment of the interbody spinal implant illustrated in FIG. 12A.
Figure 13B:
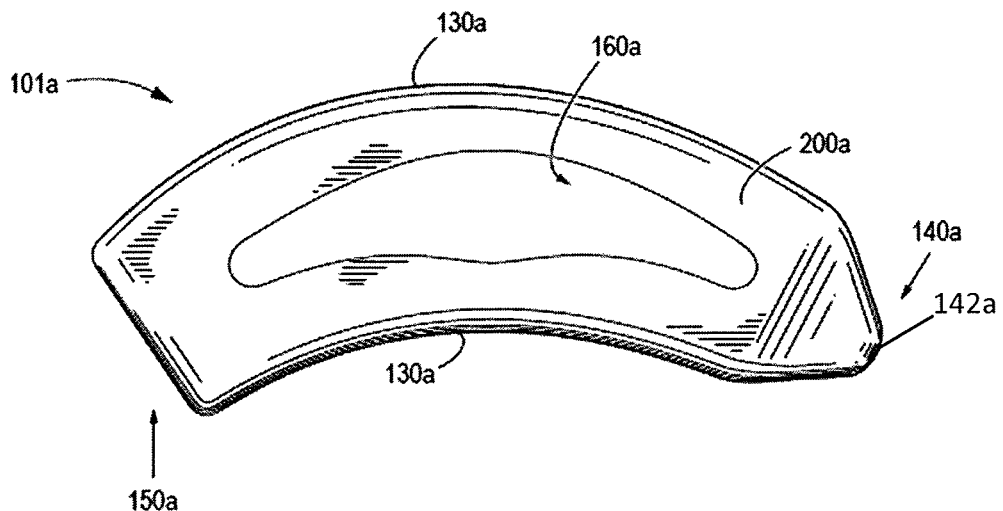
FIG. 13B is a top view of the interbody spinal implant illustrated in FIG. 13A.

In addition, the implant 1, 101, 101a, 201, and 301 may comprise some or all of the following implant features alone or in combination. The implant 1, 101, 101a, 201, and 301 may include smooth, rounded, or both smooth and rounded lateral sides 30 and posterior-lateral corners. As best shown in FIG. 12B and FIGS. 13A and 13B, the anterior portion 140, 140a may have a tapered nose 142, 142a to facilitate insertion of the implant 101, 101a. To further facilitate insertion, the implant 101 may have chamfers 106 at the corners of its posterior portion 150. The chamfers 106 prevent the implant 101 from catching upon insertion, risking potential damage such as severed nerves, while still permitting the implant 101 to have a sharp edge 108.

The implant 1, 101, 101a, 201, and 301 may include an opening 90, 190, 190a, 290, 390, for example, in the anterior portion 40, 140, 140a, 240, and 340. The posterior portion 50, 150, 150a, 250, and 350 may have a similarly shaped opening 90, 190, 190a, 290, 390 (not shown). In some aspects, only the anterior portion 40, 140, 140a, 240, and 340 has the opening 90, 190, 190a, 290, 390 while the posterior portion 50 has an alternative opening 92 (which may have a size and shape different from the opening 90, 190, 190a, 290, 390).

The opening 90, 190, 190a, 290, 390 has a number of functions. One function is to facilitate manipulation of the implant 1, 101, 101a, 201, and 301 by the caretaker. Thus, the caretaker may insert a surgical tool into the opening 90, 190, 190a, 290, 390 and, through the engagement between the surgical tool and the opening 90, 190, 190a, 290, 390, manipulate the implant 1, 101, 101a, 201, and 301. The opening 90, 190, 190a, 290, 390 may be threaded to enhance the engagement. A suitable surgical tool, such as a distractor (not shown), may be selected by one of ordinary skill in the art.

The implant 101, 101a may also have an Implant Holding Feature (IHF) 194, 194a instead of or in addition to the opening 190, 190a. As illustrated in FIGS. 12A and 13A, the IHF 194, 194a is located proximate the opening 190, 190a in the posterior portion 150, 150a. In this particular example, the IHF 194, 194a is a U-shaped notch. Like the opening 190, 190a, the IHF 194, 194a has a number of functions, one of which is to facilitate manipulation of the implant 101, 101a by the caretaker. Other functions of the opening 190, 190a and the IHF 194, 194a are to increase visibility of the implant 101, 101a during surgical procedures and to enhance engagement between bone graft material and adjacent bone.

As illustrated in FIG. 12A, the posterior portion 150 of the implant 101 may be substantially flat. Thus, the posterior portion 150 provides a face that can receive impact from a tool, such as a surgical hammer, to force the implant 101 into position.

The implant 1, 101, 101a, 201, and 301 may be provided with a solid rear wall 242. The rear wall 242 may extend the entire width of the implant body and nearly the entire height of the implant body. Thus, the rear wall 242 can essentially close the anterior portion 40, 140, 140a, 240, and 340 of the implant 1, 101, 101a, 201, and 301. The rear wall 242 may offer one or more of several advantages, including reinforcement of the implant 1, 101, 101a, 201, and 301 and improved bone graft containment. In the cervical application, it may be important to prevent bone graft material from entering the spinal canal.

The implant 1, 101, 101a, 201, and 301 may also have a lordotic angle to facilitate alignment. Depending on the type of implant 1, 101, 101a, 201, and 301, one lateral side 30, 130, 130a, 230, and 330 is preferably generally greater in height than the opposing lateral side 30, 130, 130a, 230, and 330 or the anterior portion 40, 140, 140a, 240, and 340 may be generally greater in height than the opposing posterior portion 50, 150, 150a, 250, and 350. Therefore, the implant 1, 101, 101a, 201, and 301 may better compensate for the generally less supportive bone found in certain regions of the vertebral endplate. As much as seven to fifteen degrees of lordosis (or more) may be built into the implant 1, 101, 101a, 201, and 301 to help restore cervical balance.

To enhance movement resistance and provide additional stability under spinal loads in the body, the implant 1, 101, and 301 may comprise one or more anti-expulsion edges 8, 108, and 308 that tend to "dig" into the end-plates slightly and help to resist expulsion. The anti-expulsion edges 8, 108, and 308 may be present on the top surface 10, 110, and 310; the bottom surface 20, 120, and 320; or both surfaces of the implant 1, 101, and 301 (or the top surface 81 of the integration plate 82 when present). Each anti-expulsion edge 8, 108, and 308 may protrude above the plane of the top surface 10, 110, and 310 or bottom surface 20, 120, and 320, with the amount of protrusion increasing toward the anterior face 40, 140, and 340 and the highest protrusion height at the anterior-most edge of the top surface 10, 110, and 310 or bottom surface 20, 120, and 320.

An anti-expulsion edge 8, 108, and 308 may be oriented toward the anterior portion 40, 140, and 340, or the posterior portion 50, 150, and 350, or either of the opposing lateral sides 30, 130, and 330. The orientation of the anti-expulsion edge 8, 108, and 308 may depend on the intended orientation of the implant 1, 101, and 301 when it has been implanted between vertebrae in the patient.

The screws 72, screw retaining members, and implant 1, 101, 101a, 201, and 301 may be composed of any suitable biocompatible material. In an exemplary embodiment, the screws 72, screw retaining members, implant 1, 101, 101a, 201, and 301, or all are formed of metal. The metal may be coated or not coated. Suitable metals, such as titanium, aluminum, vanadium, tantalum, stainless steel, and alloys thereof, may be selected by one of ordinary skill in the art. In a preferred embodiment, the implant 1, 101, 101a, 201, and 301 includes at least one of titanium, aluminum, and vanadium, without any coatings. In a more preferred embodiment, the implant 1, 101, 101a, 201, and 301 is comprised of titanium or a titanium alloy. An oxide layer may naturally form on a titanium or titanium alloy. Titanium and its alloys are generally preferred for certain embodiments of the present invention due to their acceptable, and desirable, strength and biocompatibility. In this manner, certain embodiments of the present interbody spinal implant 1, 101, 101a, 201, and 301 may have improved structural integrity and may better resist fracture during implantation by impact.

In the case of a composite, the implant 1, 101, 101a, 201, and 301 may further comprise another suitable biocompatible material. For example, in the case of a composite implant 1, 101, 101a, 201, and 301 with one or more integration plates 82, 382, the integration plates 82, 382 may be formed from the metals described above and the body 2 of the implant 1, 101, 101a, 201, and 301 may be formed from a plastic, polymeric, or composite material. For example, suitable polymers may comprise silicones, polyolefins, polyesters, polyethers, polystyrenes, polyurethanes, acrylates, and co-polymers and mixtures thereof. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Roughened Surface Topography

The top surface 10, 110, 110a, 210, and 310 or bottom surface 20, 120, 120a, 220, and 320 of the implant 1, 101, 101a, 201, and 301 (or the top surface 81 of the integration plate 82 when present) may each have a roughened surface topography 80, 180, 180a, 280, 380, without sharp teeth that risk damage to bone structures, adapted to grip bone through friction generated when the implant 1, 101, 101a, 201, and 301 is placed between two vertebrae, inhibit migration of the implant 1, 101, 101a, 201, and 301, and optionally promote biological and chemical fusion (e.g., a biostimulating effect).

The ability to achieve spinal fusion is directly related to the available vascular contact area over which fusion is desired, the quality and quantity of the fusion mass, and the stability of the interbody spinal implant 1, 101, 101a, 201, and 301. The implants 1, 101, 101a, 201, and 301 allow for improved seating over the apophyseal rim of the vertebral body and better utilize this vital surface area over which fusion may occur and may better bear the considerable biomechanical loads presented through the spinal column with minimal interference with other anatomical or neurological spinal structures. The implants 1, 101, 101a, 201, and 301 may allow for improved visualization of implant seating and fusion assessment. The roughened surface topography 80, 180, 180a, 280, 380 helps to facilitate osteointegration (e.g., formation of a direct structural and functional interface between the artificial implant and living bone or soft tissue) with the surrounding living bone.

It is generally believed that the surface of an implant 1, 101, 101a, 201, and 301 determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells upon the implant surface. Still further, it appears that these cells attach more readily to relatively rough surfaces rather than smooth surfaces. In this manner, a surface may be bioactive due to its ability to stimulate cellular attachment and osteointegration. The roughened surface topography 80, 180, 180a, 280, 380 described in this document may better promote the osteointegration of certain embodiments of the present invention. The roughened surface topography 80, 180, 180a, 280, 380 may also better grip the surfaces of the vertebral endplate and inhibit implant migration upon placement and seating.

The implant 1, 101, 101a, 201, and 301 may include the roughened surface topography 80, 180, 180a, 280, 380 on at least a portion of one or more integration surfaces. As used in this document, the integration surface is the surface at least partially in contact with the vertebral or bone structure (e.g., the top surface 10, 110, 110a, 210, and 310 or bottom surface 20, 120, 120a, 220, and 320 of the implant 1, 101, 101a, 201, and 301 or the top surface 81, 381 of the integration plate 82, 382 when present).

The roughened surface topography 80, 180, 180a, 280, 380 preferably contains predefined surface features that (a) engage the vertebral endplates with a friction fit and, following an endplate preserving surgical technique, (b) attain initial stabilization, and (c) benefit fusion. The composition of the vertebral endplate is a thin layer of notch-sensitive bone that is easily damaged by features (such as teeth) that protrude sharply from the surface of traditional implants. Avoiding such teeth and the attendant risk of damage, the roughened surface topography 80, 180, 180a, 280, 380 does not have teeth or other sharp, potentially damaging structures; rather, the roughened surface topography 80, 180, 180a, 280, 380 may have a pattern of repeating features of predetermined sizes, smooth shapes, and orientations. By "predetermined" is meant determined beforehand, so that the predetermined characteristic of the surface must be determined, i.e., chosen or at least known, before use of the implant 1, 101, 101a, 201, and 301.

The roughened surface topography 80, 180, 180a, 280, 380 may be comprised of macro features, micro features, and nano features. For example, the roughened surface topography 80, 180, 180*a*, 280, 380 may be obtained by combining separate macro processing, micro processing, and nano processing steps. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters. The term "nano" typically means one billionth ($10^{-9}$); for example, in the present application, dimensions measured in nanometers (nm) which correspond to $10^{-9}$ meters.

The shapes of the frictional surface protrusions of the roughened surface topography 80, 180, 180*a*, 280, 380 may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding sharp edges. Other shapes are possible, such as ovals, polygons (including rectangles), and the like. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

Figure 17:
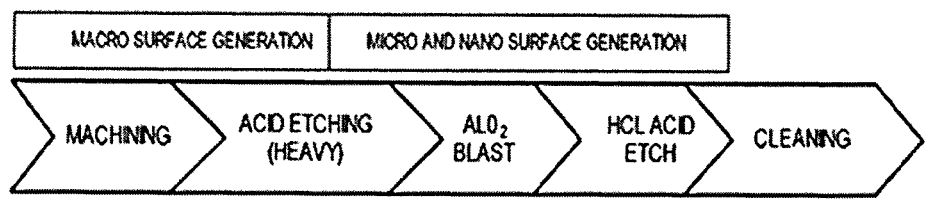
FIG. 17 illustrates examples of types of process steps that can be used to form macro, micro, or nano processes.

FIG. 17 illustrates one set of process steps that can be used to form the roughened surface topography 80, 180, 180*a*, 280, 380 according to an embodiment of the present invention. First, the part is machined, for example, from a bar stock comprising titanium, and a rough clean may be provided to remove any contaminants from machining Second, the part may undergo a heavy acid etching (e.g., masked etching). Next, the part may undergo an abrasive blast, for example, using an alumina abrasive. The part may also undergo another acid etch, for example, with a solution comprising hydrochloric acid. Finally, the part may undergo a cleaning (e.g., with water and optionally a detergent). As illustrated, there may be some overlap in the processes that can be applied to form each of the three types of features (macro, micro, and nano). For example, acid etching can be used to form the macro features, then the same or a different acid etching process can be used to form the micro features.

(a) Macro Features

The macro features of the roughened surface topography 80, 180, 180*a*, 280, 380 are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove portions of the surface (e.g., from the base material that was used to form the implant 1, 101, 101*a*, 201, and 301). Suitable subtractive techniques may include, for example, machining (e.g., machine tools, such as saws, lathes, milling machines, and drill presses, are used with a sharp cutting tool to physically remove material to achieve a desired geometry) or masked etching (e.g., portions of the surface are protected by a "masking" material which resists etching and an etching substance is applied to unmasked portions). The patterns may be organized in regular repeating patterns and optionally overlap each other. In a preferred embodiment, the macro features may be formed in three, sequential steps.

The macro features may be produced by a heavy masked etching process, for example. Before etching, the surface may be cleaned and optionally blasted with an abrasive (e.g., alumina) in the areas to be chemically textured. Certain areas may be masked in a pattern using an etch resist and cured. The surface may then be chemically milled, for example, using a composition comprising hydrofluoric acid. The maskant and chemical milling may be repeated any number of times necessary to produce the desired pattern and etching depth. After the final etching process, the maskant may be removed and the part may be cleaned. The surface may also be passivated, for example, using an aqueous solution comprising nitric acid. The part may be cleaned and rinsed with water.

The macro features may be formed, for example, using three cut patterns. Specifically, a first cut pattern of the macro features may be formed in a surface (e.g., the top surface 10, 110, 110*a*, 210, and 310). The "cut 1" features of the first cut pattern may cover about 20% of the total area of the surface, for example, leaving about 80% of the original surface remaining. The range of these percentages may be about ±20%, preferably ±10%, and more preferably about ±5%. The "cut 1" features of the first cut pattern do not have any undercuts. In one embodiment, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the roughened surface topography 80, 180, 180a, 280, 380.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In an embodiment of the invention, these "cut 3" features may have the largest diameter and least depth of the macro features that are formed during the sequential process steps.

(b) Micro Features

After the macro features are formed, additional process steps may be sequentially applied, in turn, to form the micro surface features (e.g., on the order of micrometers) of the roughened surface topography 80, 180, 180a, 280, and 380. The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are removed by masked or unmasked etching, such as acid etching. For example, portions of the surface, including portions of the surface exposed by the macro step(s) described above, may be exposed to abrasive blasting, chemical etching, or both. In an exemplary embodiment, the micro process includes an acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. Preferably, the acid etching uses an aqueous solution comprising hydrochloric acid. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features. For example, the roughened surface topography 80, 180, 180a, 280, and 380 may be obtained via the repetitive masking and chemical or electrochemical milling processes described in U.S. Pat. No. 5,258,098; No. 5,507,815; No. 5,922,029; and No. 6,193,762, the contents of which are incorporated by reference into this document, in their entirety, and for all purposes.

By way of example, an etchant mixture of at least one of nitric acid and hydrofluoric acid may be repeatedly applied to a titanium surface to produce an average etch depth of about 0.53 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

In one embodiment, the micro features are created by abrasive or grit blasting, for example, by applying a stream of abrasive material (such as alumina, sand, and the like) to the surface. In an exemplary embodiment, the micro features are created, at least partially, with an aqueous hydrochloric acid etching step and at least partially with an $AlO_2$ blasting step. Patterns may be organized in regular repeating patterns and optionally overlap each other. After the micro features are formed, it is possible that less than about 3% of the original surface remains. The range of that percentage may be about ±1%.

(c) Nano Features

After the macro features and micro features are formed, additional process steps may be sequentially applied, in turn, to form the nano surface features (e.g., on the order of nanometers) of the roughened surface topography 80, 180, 180a, 280, and 380. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are removed by masked or unmasked etching. For example, portions of the surface, including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the weight percent of the solution.

The acid solution may be applied to the surface using any suitable mechanism or techniques known in the art, for example, immersion, spraying, brushing, and the like. In an exemplary embodiment, the acid solution is applied by immersing the entire part in the solution. It is also contemplated that the surface may be immersed in the acid solution alone or in combination with the assembled implant 1, 101, 101a, 201, and 301. If desired, certain areas of the surface or the implant 1, 101, 101a, 201, and 301 may be masked in patterns or to protect certain portions of the implant 1, 101, 101a, 201, and 301. The acid solution may be heated when it is applied. For example, the solution may be heated to a temperature of about 150-250° F. (66-121° C.), preferably about 200-210° F. (93-99° C.), and most preferably about 205° F. (96° C.). The solution may also be applied for any suitable period of time. For example, the solution may be applied for a period of time of about 5-30 minutes, preferably about 15-25 minutes, and more preferably about 20 minutes.

After the acid solution is applied, the acid solution may be removed, for example, by rinsing with water (e.g., deionized water). The surface or entire implant 1, 101, 101a, 201, and 301 may be subsequently dried. The surface may be dried using any suitable mechanism or techniques known in the art, for example, by heating in an oven (e.g., a dry oven). The surface may be heated to a temperature of about 110-130° F. (43-54° C.), preferably about 120-125° F. (49-52° C.), and most preferably about 122.5° F. (50° C.). The surface may be heated for any suitable period of time, for example about 30-50 minutes, preferably about 35-45 minutes, and more preferably about 40 minutes. After heating, the surface may be cooled to room temperature, for example.

It is contemplated that the nano features may also be created by the abrasive or grit blasting, for example, described for the micro processing step. Patterns may be organized in regular repeating patterns and optionally overlap each other. The nano features may also be achieved by tumble finishing (e.g., tumbling) the part or the implant 1, 101, 101a, 201, and 301. Suitable equipment and techniques can be selected by one of ordinary skill in the art. For example, a barrel may be filled with the parts or implants 1, 101, 101a, 201, and 301 and the barrel is then rotated. The parts or implants 1, 101, 101a, 201, and 301 may be tumbled against themselves or with steel balls, shot, rounded-end pins, ballcones, or the like. The tumbling process may be wet (e.g., with a lubricant) or dry. After the nano features are formed, it is possible that less than about 1% of the original surface remains. For example, after the nano features are formed, the roughened surface topography 80, 180, 180a, 280, and 380 may cover substantially all of the top surface 10, 110, 110a, 210, and 310 and/or bottom surface 20, 120, 120a, 220, and 320 of the implant 1, 101, 101a, 201, and 301.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

As should be readily apparent to a skilled artisan, the process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the roughened surface topography 80, 180, 180a, 280, and 380 of the implant 1, 101, 101a, 201, and 301 should be oriented in opposition to the biologic forces on the implant 1, 101, 101a, 201, and 301 and to the insertion direction. In one particular embodiment, for example, the pattern of the roughened surface topography 80, 180, 180a, 280, and 380 may be modeled after an S-shaped tire tread.

Roughness Parameters

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 18:
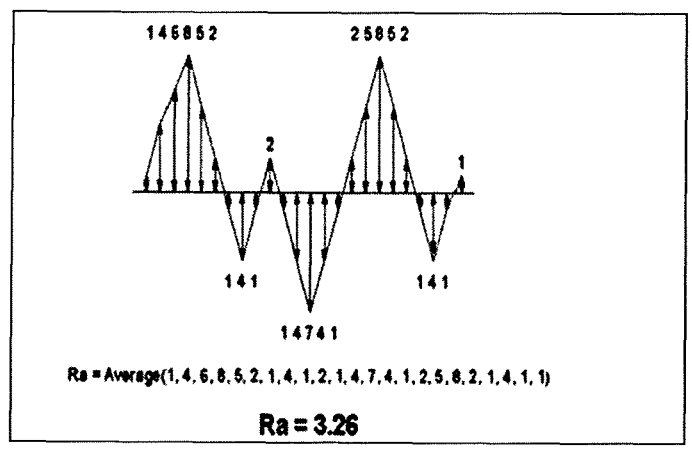
FIG. 18 graphically represents the average amplitude, Ra.

In practice, "Ra" is the most commonly used roughness parameter. It is the arithmetic average height. Mathematically, Ra is computed as the average distance between each roughness profile point and the mean line. In FIG. 18, the average amplitude is the average length of the arrows.

In mathematical terms, this process can be represented as $$Ra = \frac{1}{n}\sum_{i=1}^{n}|y_i|$$

2. Average Peak-to-Valley Roughness Rz

Figure 19:
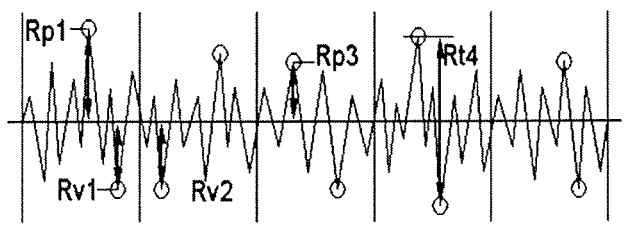
FIG. 19 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 19.

3. Maximum Peak-to-Valley Height Rmax

Figure 20:
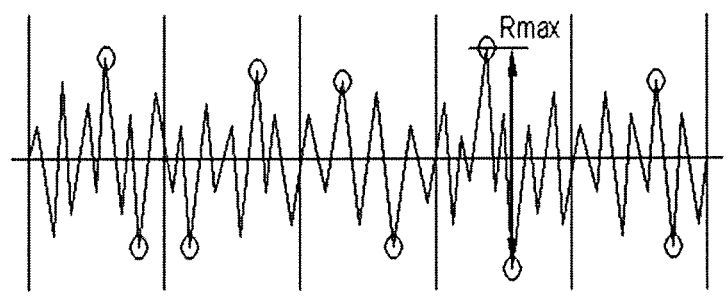
FIG. 20 graphically represents the maximum peak-to-valley height, Rmax.

The maximum peak-to-valley height, Rmax, is the maximum peak-to-valley distance in a single sampling length—as illustrated in FIG. 20.

4. Total Peak-to-Valley of Waviness Profile Wt

Figure 21:
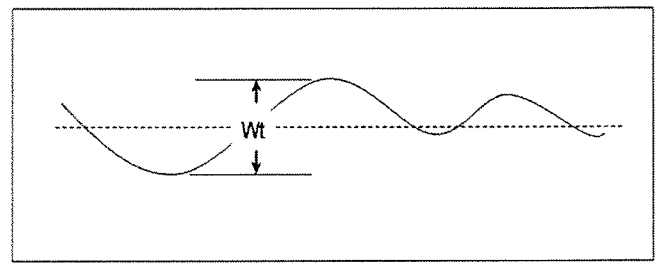
FIG. 21 graphically represents the total peak-to-valley of waviness profile.

The total peak-to-valley of waviness profile (over the entire assessment length) is illustrated in FIG. 21.

5. Mean Spacing Sm

Figure 22:
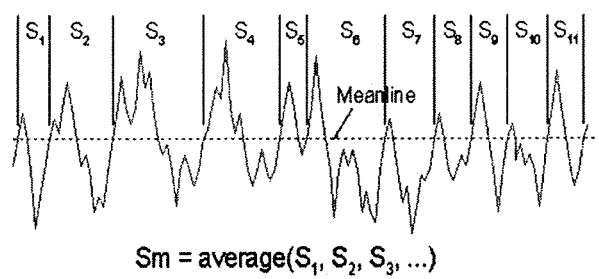
FIG. 22 graphically represents the mean spacing, Sm.

The mean spacing, Sm, is the average spacing between positive mean line crossings. The distance between each positive (upward) mean line crossing is determined and the average value is calculated, as illustrated in FIG. 22.

The parameters Sm, Rmax, and Ra can be used define the surface roughness following formation of each of the three types of features macro, micro, and nano. Such data are provided in Table 1 below.

TABLE 1

EXAMPLE DATA BY PROCESS STEP

| | Size (Sm) | Depth (Rmax) | Roughness (Ra) |
|---|---|---|---|
| Surface Feature Size and Roughness (Metric): Macro (μm) | | | |
| Max. | 2,000 | 500 | 200 |
| Min. | 400 | 40 | 20 |
| Avg. | 1,200 | 270 | 110 |
| Surface Feature Size and Roughness (Metric): Micro (μm) | | | |
| Max. | 400 | 40 | 20 |
| Min. | 20 | 2 | 1 |
| Avg. | 210 | 11 | 5.5 |
| Surface Feature Size and Roughness (Metric): Nano (μm) | | | |
| Max. | 20 | 2 | 1 |
| Min. | 0.5 | 0.2 | 0.01 |
| Avg. | 10.25 | 1.1 | 0.505 |

From the data in Table 1, the following preferred ranges (all measurements in microns) can be derived for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 20-200, with a range of 50-150 preferred and a range of 100-125 most preferred.

The following preferred ranges (all measurements in microns) can be derived for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, with a range of 2-15 preferred and a range of 4-10 most preferred.

The following preferred ranges (all measurements in microns) can be derived for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-1, with a range of 0.02-0.8 preferred and a range of 0.03-0.6 most preferred.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101a, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101a, 201, and 301 into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, the interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1, 101, 101a, 201, and 301 to accept and share stress transmitted from the endplates. In addition, spared endplates minimize the concern that BMP might erode the cancellous bone.

The interbody spinal implant 1, 101, 101a, 201, and 301 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, the surface roughened topography 80, 180, 180a, 280, 380 may lessen the risk of excessive bone removal during distraction as compared to implants having teeth, ridges, or threads currently known in the art even in view of a press-fit surgical distraction method. Nonetheless, once implanted, the interbody surgical implant 1, 101, 101a, 201, and 301 may provide secure seating and prove difficult to remove. Thus, certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration at one or both of the outer surfaces (e.g., top 10 or bottom 20 surfaces).

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. The interbody spinal implant 1, 101, 101a, 201, and 301, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical techniques have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1, 101, 101*a*, 201, and 301. Once adequate distraction is achieved, the surgeon prepares the end-plate with a rasp. There is no secondary instrumentation required to keep the disc space distracted while the implant 1, 101, 101*a*, 201, and 301 is inserted, as the implant 1, 101, 101*a*, 201, and 301 has sufficient mechanical strength that it is impacted into the disc space. In fact, the height of the implant 1, 101, 101*a*, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101*a*, 201, and 301 has adequate strength to allow impact, and the sides of the implant 1, 101, 101*a*, 201, and 301 may have smooth surfaces to allow for easy implantation and, specifically, to prevent binding of the implant 1, 101, 101*a*, 201, and 301 to soft tissues during implantation.

The invention encompasses a number of different implant 1, 101, 101*a*, 201, and 301 configurations, including a composite implant formed of top and optional bottom plates (components), for example, made out of titanium. The integration surfaces exposed to the vertebral body have a roughened surface topography 80, 180, 180*a*, 280, 380 to allow for bony in-growth over time, and to provide resistance against expulsion. The top and bottom titanium plates may be assembled together with the implant body. The net result is a composite implant that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101*a*, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A screw assembly for retaining a screw in a hole in a spinal implant, comprising a screw comprising a head and a shaft, and a self-deploying screw retention member positioned beneath the head of the screw and surrounding the shaft of the screw, wherein the screw retention member comprises a thermal-reactive shape memory metal, and the screw retention member is maintained at a contracted position at a temperature below room temperature, which contracted position is adapted to permit insertion of the screw assembly through a hole in a spinal implant, and expands into an expanded position when the screw retention member attains a transformation temperature of from about 30° C. to about 37° C., which expanded position is adapted for retaining the screw assembly within the hole in the spinal implant.

2. The screw assembly of claim 1, wherein the screw retention member is a coiled spring or a collar comprising a plurality of tabs.

3. The screw assembly of claim 2, wherein the screw retention member is a coiled spring having at least a portion proximate to the head of the screw, and wherein said portion has a first diameter when the coiled spring is in the contracted position and has a second diameter greater than the first diameter when the coiled spring is in the expanded position.

4. The screw assembly of claim 3, wherein the coiled spring has a first length when the coiled spring is in the contracted position and has a second length greater than the first length when the coiled spring is in the expanded position.

5. The screw assembly of claim 3, wherein said portion contacts the shaft of the screw in the contracted position and does not contact the shaft of the screw in the expanded position.

6. The screw assembly of claim 3, wherein the portion comprises an alloy of nickel and titanium.

7. The screw assembly of claim 3, wherein the portion comprises nitinol.

8. The screw assembly of claim 3, wherein the coiled spring has two points of contact with the hole when the coiled spring is in the expanded position.

9. The screw assembly of claim 2, wherein the screw retention member is a collar comprising a plurality of tabs, and wherein the tabs approximately contour to the shape of the head of the screw when the tabs are in the contracted position, and the tabs form an angle of about 80° to about 110° to the vertical axis of the shaft when the tabs are in the expanded position.

10. The screw assembly of claim 9, wherein the tabs form an angle of about 90° to the vertical axis of the shaft when the tabs are in the expanded position.

11. The screw assembly of claim 9, wherein the collar comprises an expansion gap.

12. The screw assembly of claim 9, wherein the tabs are spaced equidistantly around the circumference of the collar.

13. The screw assembly of claim 9, wherein the tabs comprise an alloy of nickel and titanium.

14. The screw assembly of claim 9, wherein the tabs comprise nitinol.

15. The screw assembly of claim 9, wherein the plurality of tabs are present on a portion of the collar having a first diameter when the collar is in the contracted position and a second diameter greater than the first diameter when the collar is in the expanded position.

16. The screw assembly of claim 2, wherein the screw retention member is a collar comprising a plurality of tabs, and wherein the plurality of tabs are present on a portion of the collar having a first diameter when the collar is in the contracted position and a second diameter greater than the first diameter when the collar is in the expanded position.

17. The screw assembly of claim 16, wherein the tabs comprise nitinol.

18. The screw assembly of claim 16, wherein the tabs comprise an alloy of nickel and titanium.

19. The screw assembly of claim 1, wherein the thermal-reactive shape memory metal comprises an alloy of nickel and titanium.

20. The screw assembly of claim 1, wherein the thermal-reactive shape memory metal comprises nitinol.

21. The screw assembly of claim 1, wherein the transformation temperature is about 37° C.

* * * * *